United States Patent
Nakagawa et al.

(10) Patent No.: US 7,996,186 B2
(45) Date of Patent: Aug. 9, 2011

(54) MEASUREMENT DATA COMMUNICATION DEVICE, INFORMATION ACQUIRING DEVICE, AND SYSTEM

(75) Inventors: Katsuya Nakagawa, Kizugawa (JP); Hiroaki Niwamoto, Nara (JP)

(73) Assignee: Sharp Kabushiki Kaisha, Osaka (JP)

( * ) Notice: Subject to any disclaimer, the term of this patent is extended or adjusted under 35 U.S.C. 154(b) by 165 days.

(21) Appl. No.: 11/932,905

(22) Filed: Oct. 31, 2007

(65) Prior Publication Data

US 2008/0109188 A1    May 8, 2008

(30) Foreign Application Priority Data

Nov. 6, 2006   (JP) ................................ 2006-300983

(51) Int. Cl.
*G06F 15/00*   (2006.01)

(52) U.S. Cl. ..................... 702/188; 607/60; 340/870.07; 340/539.12

(58) Field of Classification Search .................. 702/122, 702/131, 188; 600/373, 377, 382; 607/33, 607/60; 340/870.01, 870.07, 870.11, 539.11, 340/539.12, 539.16, 539.17; 128/903, 904
See application file for complete search history.

(56) References Cited

U.S. PATENT DOCUMENTS

| | | | | |
|---|---|---|---|---|
| 4,791,936 | A | * | 12/1988 | Snell et al. .................... 600/510 |
| 5,136,285 | A | * | 8/1992 | Okuyama ................ 340/870.11 |
| 5,704,351 | A | | 1/1998 | Mortara et al. |
| 5,799,308 | A | | 8/1998 | Dixon |
| 6,349,348 | B1 | | 2/2002 | Nishio et al. |
| 6,520,910 | B1 | | 2/2003 | Kohls |
| 2004/0181536 | A1 | | 9/2004 | Matsuura et al. |
| 2004/0199056 | A1 | * | 10/2004 | Husemann et al. ........... 600/300 |
| 2006/0031378 | A1 | | 2/2006 | Vallapureddy et al. |
| 2007/0055324 | A1 | * | 3/2007 | Thompson et al. ............. 607/60 |

FOREIGN PATENT DOCUMENTS

| | | |
|---|---|---|
| DE | 101 50 364 A1 | 4/2002 |
| GB | 2 415 786 A | 1/2006 |
| JP | 1-177241 A | 7/1989 |
| JP | 6-81142 B2 | 10/1994 |
| JP | 8-6828 A | 1/1996 |
| JP | 08-329160 A | 12/1996 |
| JP | 11-306124 A | 11/1999 |
| JP | 2000-59404 A | 2/2000 |
| JP | 2001-103079 A | 4/2001 |
| JP | 2002-189852 A | 7/2002 |
| JP | 2003-67225 A | 3/2003 |
| JP | 2003-333107 A | 11/2003 |
| JP | 2005-333269 A | 12/2005 |

* cited by examiner

*Primary Examiner* — Manuel L Barbee

(74) *Attorney, Agent, or Firm* — Birch, Stewart, Kolasch & Birch, LLP

(57) ABSTRACT

A measurement data communication device for measuring a health condition of an examinee and transmitting a plurality of measurement values representing a result of the measurement, to an information acquiring device managing the measurement values, includes: communication information generating means for generating communication information in accordance with (i) an attribute definition column defining attributes of the plurality of measurement values, and (ii) a code value uniquely corresponding to the attribute definition column; measurement data generating means for generating measurement data in accordance with the code value and the plurality of measurement values; and transmitting means for transmitting the communication information and the measurement data to the information acquiring device. This makes it possible to realize a measurement data communication device and an information acquiring device, each of which (i) expresses, with one code, attributes to a plurality of measurement items of measurement data, for each measurement device; (ii) employs a different code system according to a type of measurement device; (iii) allows for free addition of a new measurement item; and the like.

12 Claims, 14 Drawing Sheets

FIG. 4

IDENTIFIED IN THE FIRST BYTE OF AH ARE COMMUNICATION METHOD FOR DATA FRAME, SERVICE, FORMAT OF DATA FIELD DESCRIBED IN ADF, AND WHETHER DIVISIONAL COMMUNICATION IS CARRIED OUT.

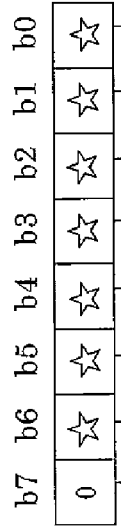

| | |
|---|---|
| COMMUNICATION IDENTIFIER | 0 : NOTIFICATION (WITHOUT VERIFICATION)<br>1 : REQUEST  2 : RESPONSE<br>3 : NOTIFICATION (WITH VERIFICATION)<br>4 : CHECK NOTIFICATION |
| DIVISION IDENTIFIER | 0 : NON-DIVISIONAL  1 : DIVISIONAL |
| DATA FORMAT IDENTIFIER | 0 : MULTI-VALUE DATA FORMAT<br>1 : SINGLE-VALUE DATA FORMAT |
| SERVICE IDENTIFIER | 0 : DEVICE REGISTRATION  1 : COMMUNICATION INFORMATION REGISTRATION<br>2 : DATA COMMUNICATION  3 : INQUIRY |
| — | RESERVED FOR FUTURE STANDARDIZATION. |

Bit7 : RESERVED FOR SYSTEM.
Bit4 : DATA FORMAT IDENTIFIER, WHICH IS IDENTIFIER DESCRIBING WHETHER DATA FORMAT OF ADF IS SINGLE-VALUE DATA FORMAT OR MULTI-VALUE DATA FORMAT.
Bit3 : DIVISION IDENTIFIER, WHICH IS AN IDENTIFIER DESCRIBING WHETHER ADF IS DIVISIONAL DATA OR NON-DIVISIONAL DATA.

FIG. 5

SEQUENCE OF BITS IS MADE UP OF SEQUENCE NUMBER FOR IDENTIFYING SOURCE DATA, LEADING IDENTIFIER FOR NOTIFYING HOW MANY FRAMES SOURCE DATA IS DIVIDED INTO, AND TRANSMISSION NUMBER FOR CHECKING ORDER OF TRANSMISSION OF DIVISIONAL FRAMES.
IN THE CASE OF CARRYING OUT RESPONSE COMMUNICATION OR CHECK NOTIFICATION COMMUNICATION, THE SEQUENCE NUMBER OF CORRESPONDING REQUEST COMMUNICATION OR NOTIFICATION (WITH VERIFICATION) COMMUNICATION IS DESCRIBED THEREIN.

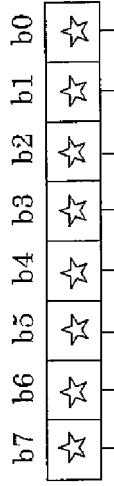

| TRANSMISSION NUMBER | 0~31 |
| SEQUENCE NUMBER | 0~3 |
| LEADING IDENTIFIER | 0 : LEADING FRAME<br>1 : SECOND OR LATER FRAMES |

Bit7: LEADING IDENTIFIER
LEADING IDENTIFIER INDICATES "0" IN THE CASE OF NON-DIVISIONAL COMMUNICATION.
IN THE CASE OF DIVISIONAL COMMUNICATION, LEADING IDENTIFIER IN LEADING FRAME INDICATES "0" AND LEADING IDENTIFIERS IN SECOND AND LATER FRAMES INDICATE "1".

Bit6, 5: SEQUENCE NUMBER
NUMBER FOR IDENTIFYING COMMUNICATION SOURCE DATA. 0 TO 3 SEQUENTIALLY APPEAR IN SEQUENCE NUMBER. AFTER 3, 0 APPEARS AGAIN.
DESCRIBE THE SAME SEQUENCE NUMBER IN FRAMES IN THE CASE OF DIVISIONAL COMMUNICATION.
DESCRIBE SEQUENCE NUMBER CORRESPONDING TO REQUEST COMMUNICATION OR NOTIFICATION (WITH VERIFICATION) COMMUNICATION, IN THE CASE OF RESPONSE COMMUNICATION OR CHECK NOTIFICATION COMMUNICATION.
NOTE THAT HCD APPLICATION PREPARES SEQUENCE NUMBER FOR EACH HMD APPLICATION WITH WHICH HCD APPLICATION COMMUNICATES. HCD APPLICATION USES SEQUENCE NUMBER CORRESPONDING TO HMD APPLICATION FOR EACH COMMUNICATION.

Bit4, 3, 2, 1: TRANSMISSION NUMBER
IN THE CASE OF NON-DIVISIONAL COMMUNICATION, TRANSMISSION NUMBER INDICATES 0. TRANSMISSION NUMBER IS RENDERED IN DESCENDING MANNER TO DIVISIONAL FRAMES IN ORDER FROM FRAME TO BE TRANSMITTED FIRST TO FRAME TO BE TRANSMITTED LAST SUCH THAT TRANSMISSION NUMBER 0 IS RENDERED TO THE LAST FRAME. HENCE, THE TOTAL NUMBER OF DIVISIONAL FRAMES IS (TRANSMISSION NUMBER WHEN LEADING IDENTIFIER INDICATES 0) +1.

FIG. 6

DATA FIELD OF SINGLE-VALUE DATA FORMAT
DL IS DESCRIBED IN THE FIRST TWO BYTES IN DATA FIELD. VALUE OF DL REPRESENTS TOTAL LENGTH OF DATA FIELD. IN CASES WHERE DV IS m BYTE, VALUE OF DL IS m + 3.
BN IS DESCRIBED IN THE THIRD BYTE FROM THE FIRST ONE, AND OCCUPIES ONE BYTE.
DV IS DESCRIBED IN THE FOURTH OR LATER BYTE FROM THE FIRST ONE.
NOTE THAT DL AND DV ARE DESCRIBED IN ACCORDANCE WITH BIG ENDIAN.

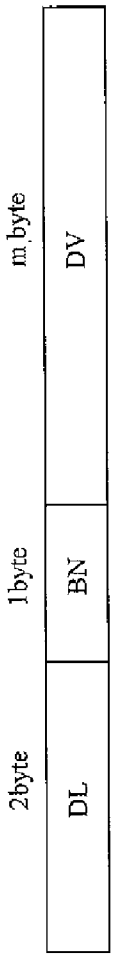

FIG. 7

DATA FIELD OF MULTI-VALUE FORMAT
DL IS DESCRIBED IN THE FIRST TWO BYTES IN DATA FIELD. VALUE OF DL REPRESENTS TOTAL LENGTH OF DATA FIELD. IN CASES WHERE DV IS m BYTE, VALUE OF DL IS m + 4.
DD IS DESCRIBED IN THE THIRD BYTE FROM THE FIRST ONE, AND OCCUPIES ONE BYTE.
CD IS DESCRIBED IN THE FOURTH BYTE FROM THE FIRST ONE, AND OCCUPIES ONE BYTE.
DV IS DESCRIBED IN THE FIFTH OR LATER BYTE FROM THE FIRST ONE.
NOTE THAT DL AND DV ARE DESCRIBED IN ACCORDANCE WITH BIG ENDIAN.

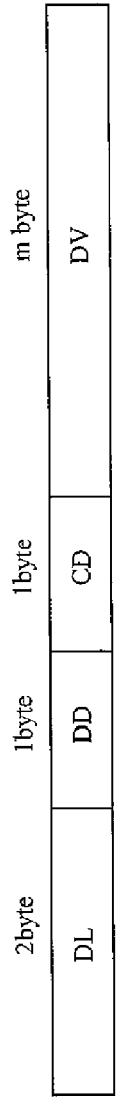

FIG. 8    LIST OF RESERVED WORDS

BN:
  0x01: VALUE INDICATING THAT UDN IS DESCRIBED.
  0x02: VALUE INDICATING THAT VERIFICATION IS DESCRIBED.

DD:
  0x01: VALUE INDICATING THAT REGISTRATION NAME IS DESCRIBED.
  0x02: VALUE INDICATING THAT NAME IS DESCRIBED.
  0x03: VALUE INDICATING THAT UNIT IS DESCRIBED.
  0x04: VALUE INDICATING THAT SCALE IS DESCRIBED.
  0x05: VALUE INDICATING THAT UDN IS DESCRIBED.

CD:
  0x10: ascii CODE
  0x20: JIS CODE
  0x30: SHIFT JIS CODE
  0x01: BINARY CODE REGISTRATION NAME UPON DEVICE REGISTRATION :
"NedohhcVersion1.1" : VALUE INDICATING VERSION NUMBER OF PROTOCOL USED IN HEALTH MEASURING DEVICE.
"Manufacture" : CHARACTER STRING DEFINING BENDER NAME.
"ModelName" : CHARACTER STRING DEFINING PRODUCT NAME.
"ModelNumber" : CHARACTER STRING DEFINING MODEL NUMBER.
"UDN" : CHARACTER STRING DEFINING UDN.
"FriendlyMachineName" : CHARACTER STRING DEFINING DEVICE SIMPLE NAME.
"Deregister" : CHARACTER STRING DEFINING REGISTRATION DELETION.

FIG. 9

| STANDARD NAME (ascii) | REPRESENTATIVE UNIT | WAY OF DESCRIBING SPECIAL DV | CONTENT |
|---|---|---|---|
| PersonalID | — | | PERSONAL IDENTIFIER |
| MeasurementTime | yyMMddhhmm | | MEASUREMENT TIME |
| CurrentTime | yyMMddhhmm | | CURRENT TIME |
| AllUDN | | [ ( UDN DESCRIPTION WITH DD SET AT 0x05. ) ] | ALL REGISTERED UDNS. |
| SelfDiagnosis | — | "trouble/normal" | RESULT OF DIAGNOSIS ON DEVICE OPERATION. |
| OperatingCondition | | "running, intermittent, sleep" | STATUS OF OPERATION CONDITION OF DEVICE |
| BatteryCharge | % | | BATTERY CHARGE RATE |
| BatteryLife | yyMMddhhmm | | ESTIMATED TIME AT WHICH BATTERY RUNS OUT. |
| NetworkFailure | | "trouble/normal" | CONDITION OF FAILURE IN COMMUNICATION WITH SERVER. |
| GwServerError | — | [ (DATA RECEPTION TIME) (ADF UPON DATA COMMUNICATION) ] | ERROR LOG IN COMMUNICATION BETWEEN GW AND SERVER. |
| ServerRegister | | "reg/unreg" | CONFIRM DEVICE REGISTRATION TO SERVER. |
| Advice | | | ADVICE TO USER |
| Ask-a-doc | | | QUESTION FROM USER |

FIG. 10

| STANDARD NAME (ascii) | REPRESENTATIVE UNIT | WAY OF DESCRIBING SPECIAL DV | CONTENT |
|---|---|---|---|
| Sos | | | EMERGENCY REPORT. |
| FriendlyUserName | — | | USER SIMPLE NAME |
| Age | — | | AGE |
| BirthDate | yyyyMMdd | | DATE OF BIRTH |
| Sex | — | "male/female" | SEX |
| BodyHeight | m | | HEIGHT |
| BodyTemp | °C | | BODY TEMPERATURE |
| UrineSugar | mg/dL | | URINE SUGAR VALUE |
| SysBP | mmHg | | MAXIMUM BLOOD PRESSURE |
| DiasBP | mmHg | | A MINIMUM BLOOD PRESSURE |
| MeanBP | mmHg | | AVERAGE BLOOD PRESSURE |
| HeartRate | 1/min | | HEART RATE |
| BodyWeight | kg | | BODY WEIGHT |
| BodyFat | % | | BODY FAT PERCENTAGE |
| BloodGlucose | mg/dL | | BLOOD GLUCOSE LEVEL |

FIG. 11

V FIELD
VALUE OF BN IS 0x02.
IN FIRST BYTE OF DV, RESPECTIVE RESULTS OF ERROR CHECK AND JUDGMENT PROCESS ARE DESCRIBED.
IT IS JUDGED THAT THERE IS NO ERROR, IN CASES WHERE COMMUNICATION METHOD AND SERVICE DESCRIBED IN AH OF RECEIVED DATA FRAME IS IN CONFORMITY WITH SOURCE AE, WHERE DATA FORMAT IDENTIFIER SUPPOSED TO BE USED IN THE COMMUNICATION METHOD AND SERVICE IS DESIGNATED, AND WHERE TOTAL OF DATA LENGTHS (VALUES OF DLS) OF RESPECTIVE DATA FIELDS DESCRIBED IN ADF COINCIDES WITH DATA LENGTH OF ADF
IN SECOND AND LATER BYTES, UNREGISTERED BN IS DESCRIBED.

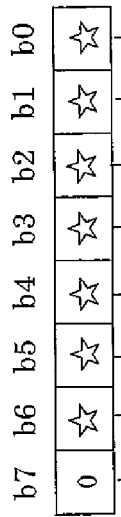

| ERROR CHECK IDENTIFIER | 0 : NO ERROR<br>1 : ERROR |
| COMMUNICATION INFORMATION REGISTRATION JUDGMENT IDENTIFIER | 0 : REGISTERED<br>1 : UNREGISTERED |
| DEVICE REGISTRATION JUDGMENT IDENTIFIER | 0 : REGISTERED  1 : UNREGISTERED<br>2 : PARTIALLY REGISTERED |
| — | RESERVED FOR FUTURE STANDARDIZATION |

FIG. 12

EXTENSION OF RESERVED WORDS

DD:
   0x06: VALUE INDICATING THAT DATA TYPE IS DESCRIBED.
   0x07: VALUE INDICATING THAT MetricValue IS DESCRIBED.

CD:
   0x02: Nomenclature CODE
   0x03: INT-U16 CODE

RESERVED WORDS USED UPON COMMUNICATION INFORMATION REGISTRATION:
   "MetricSpecification": CHARACTER STRING DEFINING TYPE OF MEASUREMENT VALUE
   "MetricLocation": CHARACTER STRING DEFINING LOCATION OF MEASUREMENT VALUE
   "XML": XML DESCRIPTION

FIG. 13

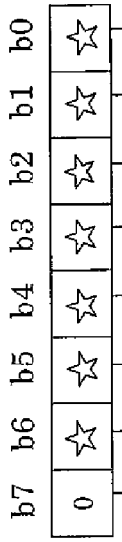

IDENTIFIED IN THE FIRST BYTE OF AH ARE COMMUNICATION METHOD FOR DATA FRAME, SERVICE, FORMAT OF DATA FIELD DESCRIBED IN ADF, AND WHETHER DIVISIONAL COMMUNICATION IS CARRIED OUT.

| | |
|---|---|
| COMMUNICATION IDENTIFIER | 0 : NOTIFICATION (WITHOUT VERIFICATION)<br>1 : REQUEST  2 : RESPONSE<br>3 : NOTIFICATION (WITH VERIFICATION)<br>4 : CHECK NOTIFICATION  5 : SETTING<br>6 : SETTING COMPLETION |
| DIVISION IDENTIFIER | 0 : NON-DIVISIONAL  1 : DIVISIONAL |
| DATA FORMAT IDENTIFIER | 0 : MULTI-VALUE DATA FORMAT<br>1 : SINGLE-VALUE DATA FORMAT |
| SERVICE IDENTIFIER | 0 : DEVICE REGISTRATION  1 : COMMUNICATION INFORMATION REGISTRATION<br>2 : DATA COMMUNICATION  3 : INQUIRY |
| — | RESERVED FOR FUTURE STANDARDIZATION. |

Bit7 : RESERVED FOR SYSTEM.
Bit4 : DATA FORMAT IDENTIFIER, WHICH IS IDENTIFIER DESCRIBING WHETHER DATA FORMAT OF ADF IS SINGLE-VALUE DATA FORMAT OR MULTI-VALUE DATA FORMAT.
Bit3 : DIVISION IDENTIFIER, WHICH IS AN IDENTIFIER DESCRIBING WHETHER ADF IS DIVISIONAL DATA OR NON-DIVISIONAL DATA.

US 7,996,186 B2

MEASUREMENT DATA COMMUNICATION DEVICE, INFORMATION ACQUIRING DEVICE, AND SYSTEM

This Nonprovisional application claims priority under 35 U.S.C. §119(a) on Patent Application No. 2006/300983 filed in Japan on Nov. 6, 2006, the entire contents of which are hereby incorporated by reference.

FIELD OF THE INVENTION

The present invention relates to (i) measurement data communication device for correlating a plurality of measurement values with a code and transmitting and receiving them, and (ii) an information acquiring device.

BACKGROUND OF THE INVENTION

A conventional communication system employing high-speed communication adopts an XML (Extensible Markup Language) or a unique standard for data communication so as to transmit data with required measurement conditions attached therewith. In such data, attributes or the like are set distinctively as data. Hence, data analysis and data conversion complying with various standards are not necessary in a system. In other words, the data itself is effective. Further, such data is analyzable by a third person, and therefore can be reused.

However, in order to transmit such data in slow communication, it takes a long time in the communication. Therefore, in a conventional communication system employing slow communication, a communication device is configured to carry out code-conversion of items of data and therefore transmit minimally required data. This data is subjected to a conversion process in a receiving end device in accordance with a standard determined in advance. As such, actually required data is created such that it can be used commonly.

Here, Japanese Unexamined Patent Publication "Tokukaihei 8-6828 (published on Jan. 12, 1996)" discloses a data processing method. Japanese PCT National Phase Unexamined Patent Publication "Tokuhyohei 9-503326 (published on Mar. 31, 1997)" discloses a method of storing and retrieving data and a device adopting the method. Japanese Unexamined Patent Publication "Tokukai 2001-103079 (published on Apr. 13, 2001)" describes a data transmitting/receiving device and a data transmitting/receiving method. Japanese Unexamined Patent Publication "Tokukai 2003-333107 (published on Nov. 21, 2003)" discloses a method of authenticating a device connectable to a network. Japanese Examined Patent Publication "Tokukouhei 6-81142 (published on Oct. 12, 1994) discloses control of an integral type device having a plurality of functions. Japanese Unexamined Patent Publication "Tokukai 2000-59404 (published on Feb. 25, 2000)" describes a home network system carrying out central control over a device terminal. Japanese Unexamined Patent Publication "Tokukai 2002-189852 (published on Jul. 5, 2002)" describes a home server system.

However, each of the conventional techniques of the above patent publications is incapable of (i) expressing, with one code, attributes to a plurality of measurement items of measurement data for each measuring device, but employing different code systems according to a type of measuring device; (ii) allowing for free addition of a new measurement item; and the like.

SUMMARY OF THE INVENTION

The present invention is made in view of the foregoing problems, and its object is to provide a measurement data communication device and information acquiring device, each of which is capable of (i) expressing, with one code, attributes to a plurality of measurement items of measurement data for each measuring device, but employing different code systems according to a type of measuring device; (ii) allowing for free addition of a new measurement item; and the like.

A measurement data communication device according to the present invention for measuring a health condition of an examinee and transmitting a plurality of measurement values representing a result of the measurement, to an information acquiring device managing the measurement values, includes: communication information generating means for generating communication information in accordance with (i) an attribute definition column defining attributes of the plurality of measurement values, and (ii) a code value corresponding to the attribute definition column; measurement data generating means for generating measurement data in accordance with the code value and the plurality of measurement values; and transmitting means for transmitting the communication information and the measurement data to the information acquiring device.

An information acquiring device according to the present invention for (i) receiving, from a measurement data communication device that measures a plurality of measurement values, a plurality of measurement values measured by the measurement data communication device and representing a health condition of an examinee and (ii) managing the plurality of measurement values, includes: receiving means for receiving (1) communication information including (i) an attribute definition column defining attributes of the plurality of measurement values and (ii) a code value corresponding to the attribute definition column, and (2) measurement data including the plurality of measurement values and the code value; attribute definition extracting storage means for extracting the attribute definition column and the code value from the received communication information and stores the attribute definition column and the code value thus extracted; and measurement value extracting means for acquiring, from the attribute definition extracting storage means, the attribute definition column corresponding to the code value, and extracting the plurality of measurement values from the received measurement data by using the attribute definition column.

A system according to the present invention includes: the measurement data communication device; and the information acquiring device.

The above structures make it possible to (i) express, with one code, attributes to a plurality of measurement items of measurement data for each measurement device; (ii) employ a different code system according to a type of measurement device; (iii) allow for free addition of a new measurement item; and the like.

With this, the measurement data communication device does not need to transmit the respective attributes of the measurement values together with the measurement values. Further, the measurement data communication device is allowed to freely correlate (i) the attribute definition column of the measurement values to be transmitted, with (ii) the code value.

Note that a measurement data communication device according to the present invention for transmitting a plurality of measurement values representing a health condition of an examinee, to an information acquiring device, may include: communication information transmitting means for transmitting, as communication information, to the information acquiring device, (i) an attribute definition column of the plurality of measurement values and (ii) a code value corresponding to the attribute definition column of the plurality of measurement values; measurement data generating means for generating measurement data in accordance with the code value and the plurality of measurement values.

Note also that an information acquiring device according to the present invention may include: a code storage means for storing an attribute definition column of a plurality of measurement values, representing a health condition, and a code value such that the attribute definition column and the code value are correlated with each other; health condition storage means for storing each measurement values as the health condition; first communication means for receiving measurement data including at least (i) the plurality of measurement values representing the health condition of the examinee and (ii) the code value corresponding to the attribute definition column of the plurality of measurement values; measurement data converting means for making reference to the code storage means in accordance with the code value contained in the measurement data, correlating the measurement data with attributes in accordance with the attribute definition column of the plurality of measurement values corresponding to the code, and storing the measurement data and the attributes in the health condition storage means.

Additional objects, features, and strengths of the present invention will be made clear by the description below. Further, the advantages of the present invention will be evident from the following explanation in reference to the drawings.

BRIEF DESCRIPTION OF THE DRAWINGS

FIG. 4 is a diagram illustrating a sequence of bits representing data items in the first byte of the application header in the present invention.

FIG. 5 is a diagram illustrating a bit sequence representing data items in the second byte of the application header in the present invention.

FIG. 6 is a diagram illustrating the structure of a data field complying with the single-value data format, in the present invention.

FIG. 7 is a diagram illustrating the structure of a data field complying with the multi-value data format, in the present invention.

FIG. 8 is a diagram illustrating a list of reserved words used for DD, CD, and the like, in the present invention.

FIG. 9 is a diagram illustrating a list of standard names used for communication information registration communication in the present invention.

FIG. 10 is a diagram illustrating the rest of the list of the standard names used for the communication information registration communication in the present invention.

FIG. 11 is a diagram illustrating a sequence of bits representing data items of the first byte of a DV of a V field in the present invention.

FIG. 12 is a diagram illustrating extensions of reserved words in an embodiment of the present invention.

FIG. 13 is a diagram illustrating a sequence of bits representing data items of the first byte of an AH for setting communication in the embodiment of the present invention.

DESCRIPTION OF THE EMBODIMENTS

<Reference Example>

[General Operation]

First, a health measuring device (measurement data communication device) makes definitions for an information acquiring device, as to (i) information to be measured by the health measuring device, and (ii) a format of data indicating the result of the measurement and to be transmitted to the information acquiring device.

Specifically, via these definitions, the health measuring device first notifies the health measuring device's manufacturer name and production number to the information acquiring device (this is called "device registration"). Then, the health measuring device notifies the information acquiring device of (i) a measurement to be carried out by the health measuring device, (ii) a format of data indicating a value that results from the measurement and to be transmitted to the information acquiring device, and (iii) a code value correlated with the format (this is called "communication information registration").

With these definitions made, the health measuring device is ready to transmit the measurement result to the information acquiring device.

Thereafter, the health measuring device actually carries out measurement, and transmits to the information acquiring device (i) the data indicating the measurement result and (ii) the code value determined in making the definitions.

In order to interpret the received data indicating the measurement result (interpret whether the data regards a weight, a pulse rate, or the like), the information acquiring device uses the code value transmitted together with the data indicating the measurement result, thereby recognizing (i) the format of the transmitted data indicating the measurement result, and (ii) the target of the measurement corresponding to the data.

In this way, the general and basic operation is carried out.

As required, the health measuring device make inquiries about information stored in the information acquiring device, such as current time and examinee information. Examples of the examinee information include age, sex, and the like.

[Schematic Structure]

The following explains one reference example for the present invention with reference to figures. Note that the same members or members having the same functions in the figures will be given the same reference symbols, and explanation thereof will not be repeated.

Figure 1:
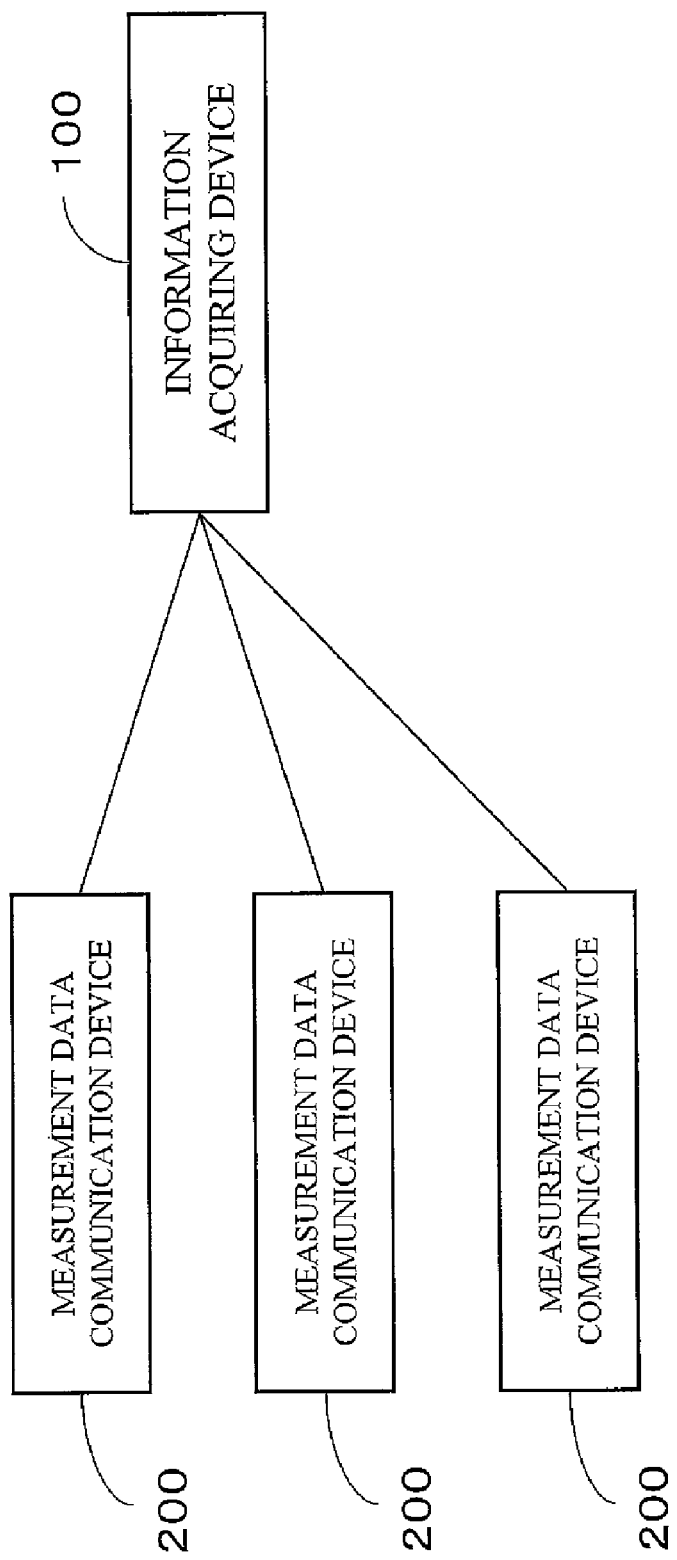
FIG. 1 is a diagram illustrating a measuring system made up of measurement data communication devices 200 and an information acquiring device 100 in the present invention.

FIG. 1 illustrates a measurement system made up of measurement data communication devices 200 and an information acquiring device 100 according to this reference example.

Each measurement data communication device is a health appliance having a function of measuring information regarding a living organism, detecting it, and outputting it to outside. Examples of the health appliance includes: a weight scale, a blood pressure meter, a blood glucose level meter, an electrocardiograph, a sphygmograph, a blood oxygen saturation meter, a thermometer, and the like.

The information acquiring device 100 is a health information managing device that collects measurement data and attributes thereof from the measurement data communication devices 200 and manages them. The information acquiring device 100 is realized by a set top box or a mobile phone.

Figure 2:
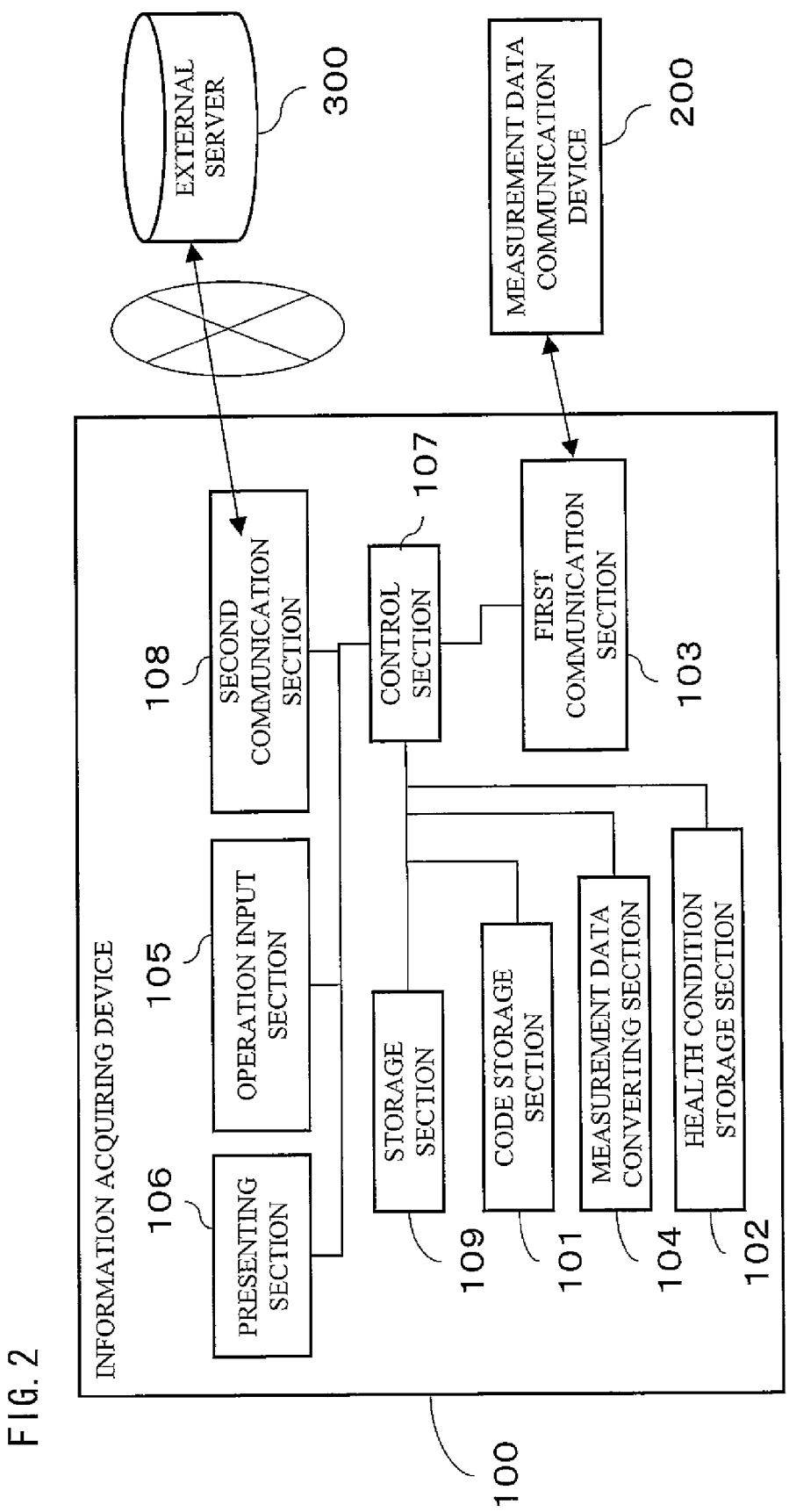
FIG. 2 is a function block diagram illustrating the information acquiring device 100 of the present invention.

FIG. 2 is a function block diagram illustrating the information acquiring device 100 according to this reference example.

Assume that the information acquiring device 100 in the present reference example is realized as a mobile phone. Note that the structure of a mobile phone is publicly known, so that only characteristic parts thereof will be described here.

A code storage section 101 (attribute definition extracting storage means) stores (i) attribute definition columns for a plurality of measurement values representing health conditions and (ii) a code value such that they are correlated with each other. A health condition storage section 102 stores each of the measurement values as data representing the health condition of an examinee. A first communication section 103 (receiving means) receives, from the measurement data communication device 200, measurement data including (i) the plurality of measurement values each indicating the health condition of the examinee and (ii) the code value corresponding to the attribute definition columns for the plurality of the measurement values. In this case, communication is carried out via (i) a short range wireless communication using IrDA (Infra-Red Data Association) or Bluetooth®, or (ii) a local area network.

The measurement data converting section 104 (receiving means) makes reference to the code storage section 101 in accordance with the code value included in the measurement data received by the first communication section 103, correlates the measurement data with an attribute in accordance with the attribute definition columns corresponding to the code and provided for the plurality of measurement values, and stores the measurement value in the health condition storage section 102. An operation input section 105 receives an examinee's operation input via a keyboard, a mouse, a microphone, or the like. A presenting section 106 presents information to the examinee via a display lamp, a liquid crystal display screen, an audio output, and the like. A control section 107 (attribute definition extracting storage means) is connected to the respective sections of the information acquiring device 100 so as to control the general operation of the information acquiring device 100.

A second communication section 108 communicates with an external server 300 so as to acquire code correlation or the like. Here, the second communication section 108 uses a wide area network such as the Internet or a public telephone network. The storage section 109 stores data and operation conditions, such as measurement conditions of the measurement data communication devices 200, operation conditions thereof, data to be registered in the external server, and data for use in updating a program for the measurement data communication device 200.

Figure 3:
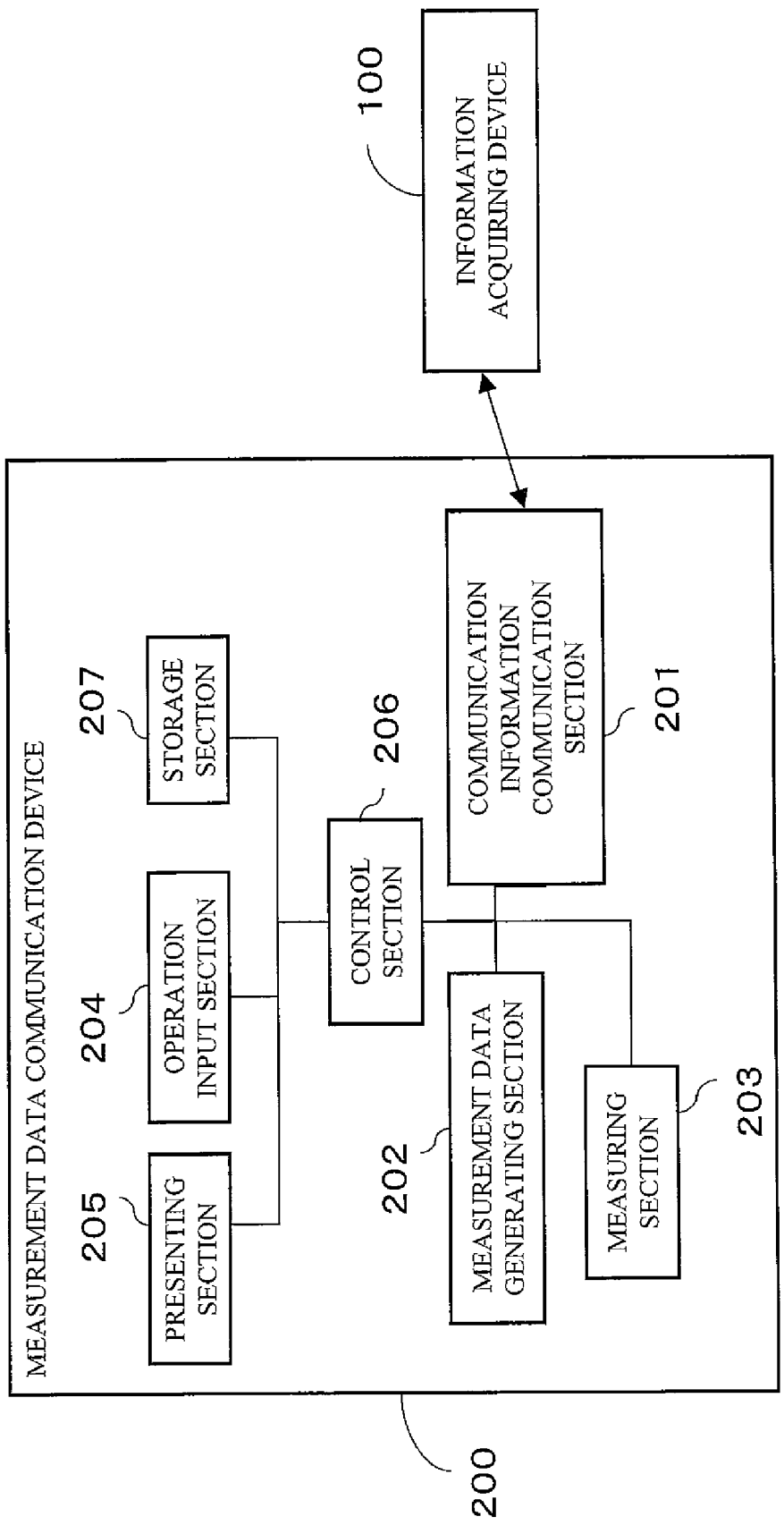
FIG. 3 is a function block diagram illustrating each measurement data communication device 200 of the present invention.

FIG. 3 is a function block diagram illustrating each of the measurement data communication devices 200 according to this reference example.

A communication information communication section 201 (transmitting means, communication information generating means) generates communication information in accordance with (i) the attribute definition columns for the plurality of measurement values and (ii) the code value corresponding to the plurality of measurement values, and transmits the communication information to the information acquiring device 100. In this case, communication is carried out via (i) a short range wireless communication using IrDA (Infra-Red Data Association) or Bluetooth®, or (ii) a local area network.

A measurement data generating section 202 (measurement data generating means) generates measurement data in accordance with the code value and the plurality of measurement values. A measuring section 203 measures various types of vital information of the examinee. An operation input section 204 receives the examinee's operation input via a keyboard, a mouse, a microphone, and the like. A presenting section 205 presents information to the examinee via a display lamp, a liquid crystal display screen, an audio output, and the like. A control section 206 (communication information generating means) is connected to the respective sections of the measurement data communication device 200 so as to control the general operation of the measurement data communication device 200. The storage section 207 stores measurement conditions of the measurement data communication device 200, operation conditions thereof, results of measurements carried out by the measuring section 203, data to be registered in the external device that makes notification to the information acquiring device 100, and data for use in updating a program for the measurement data communication device 200.

[Terms]

Next, terms used in this reference example will be defined and explained.

A health measuring device (HMD) corresponds to the measurement data communication device 200 in this reference example, and is a device for measuring health information. The health measuring device communicates with a below-described health control device.

The health control device (HCD) corresponds to the information acquiring device 100 in the present reference example, and communicates with a plurality of health measuring devices so as to manage each of the health measuring devices.

The health measuring device application is an application program to be executed so as to realize below-described operations of the health measuring device.

The health control device application is an application program to be executed so as to realize below-described operations of the health control device. A specific example of the operations is to communicate with the health measuring device application, or the like.

An application entity (AE) is a generic term for the programs of the health measuring device application and the health control device application.

A data frame is a data unit based on which the health measuring device application and the health control device application communicate with each other.

An application header (AH) is a component of the data frame. The application header has 2 bytes. FIG. 4 illustrates a sequence of bits representing items of data in the first byte. FIG. 5 illustrates a sequence of bits representing items of data in the second byte.

An application data frame (ADF) is a component of the data frame.

A communication identifier is an identifier for identifying a communication method. Explanation for the communication method will be made later in [Communication Method].

A service identifier is an identifier for identifying a service. Explanation for the service identifier will be made later in [Data Frame Structure].

A sequence number is a number for identifying a data frame used for detecting a drop frame or the like.

An error check is to check an error in the data frame.

A data field is a unit of a component of the application data frame. There are two types of data field: single-value data format and multi-value data format. FIG. 6 illustrates the structure of the single-value data format data field (DL, DV, BN will be described later). FIG. 7 illustrates the structure of the multi-value data format data field (DD, and CD will be described later).

An error check identifier is an identifier indicating the result of error check.

DL (data length) indicates the total length of a data field.

UDN (unique device name) is a name by which the health measuring device application uniquely identifies a collection of all the communication items to be transmitted. A communication item is an item that can be registered upon communication information registration.

Byte name (BN) is an identifier for uniquely identifying a communication item of the collection of communication items designated by the UDN.

DV (data value) is a region, in which the value of data is described, of the data field.

DD (data discrimination) is a data identifier, which will be described later in [Data Field].

CD (code discrimination) is a text code identifier, which will be described later in [Data Field].

FIG. 8 illustrates a list of reserved words used for DD, CD, and the like.

V (verification) field is a field in which the value of the error check identifier is described for check notification communication and response communication. In the case of data transmission from the health control device application, the respective values of a device registration judgment identifier and a communication information registration judgment identifier are additionally described therein. Further, in the case of data communication and inquiry communication, the value of an unregistered byte name is additionally described therein.

A judgment process is to check a device registration status, a communication information registration status, and a byte name and to additionally describe necessary information in the V field.

Device registration communication is one of services, and will be described later in [Device Registration Communication].

Communication information registration communication is one of services, and will be described later in [Communication Information Registration Communication].

Data communication is one of services, and will be described later in [Data Communication].

Inquiry communication is one of services, and will be described later in [Inquiry Communication].

In cases where a value indicating that a registration name is described in the DV is described in the DD, the DV has a value representing the registration name.

In cases where a value indicating that a name is described in the DV is described in the DD, the DV has a value representing the name.

In cases where a value indicating that the UDN is described in the DV is described in the DD, the DV has a character string representing the UDN.

In cases where a value indicating that a unit is described in the DV is described in the DD, the DV has a character string representing the unit.

Scale is the scale of a data value used in the data communication.

In cases where a value indicating that the scale is described in the DV is described in the DD, the DV has a character string representing the scale.

A UDN field is a data field for designating a UDN for communication information registration communication and inquiry communication.

A communication information field is made up of a plurality of continuous data fields, and serves as a unit for registering one communication information in the communication information registration communication. Each of FIG. 9 and FIG. 10 illustrates a list of standard names used in the communication information registration communication.

A personal ID is an ID for identifying a person.

A health information field is made up of a plurality of continuous data fields, and serves as a unit based on which the person's health information is transmitted or received in the data communication or the inquiry communication.

A device registration judgment identifier is an identifier for judging whether or not a device registration item has been registered.

A communication information registration judgment identifier is an identifier for judging whether or not a collection of BNs designated by the UDN registered in the device registration communication has been registered.

[Abbreviations]

In this reference example, for ease of descriptions in articles and tables, the following abbreviations are used.

That is, the health measuring device is abbreviated as "HMD", the health control device is abbreviated as "HCD", an application header is abbreviated as "AH", the application data frame is abbreviated as "ADF", and the application entity is abbreviated as "AE", the byte name is abbreviated as "BN", and the verification is abbreviated as "V".

[Data Frame Structure]

In cases where the HMD application and the HCD application make general communication with each other, the data frame is made up of (i) a header portion (AH) for controlling communication and (ii) a data portion (ADF) in which data is described.

Described in the AH are the following communication identifier, service identifier, and sequence number.

a) Communication identifier: an identifier for identifying whether the communication method employs request communication, response communication, notification (without verification) communication, notification (with verification) communication, or check notification communication.

b) Service identifier: an identifier for identifying whether the service provides device registration communication, communication information registration communication, data communication, or inquiry communication.

c) Sequence number: a number for identifying a data frame.

In the ADF, communication data is described in accordance with the format of the data field, Examples of the description in the ADF will be described later.

[Error Check]

When a data frame is received, each of the HMD application and the HCD application checks whether or not there is an error in the data frame.

[Communication Method]

Each of the HMD application and the HCD application transmits and receives a data frame in accordance with a communication method.

It is assumed that association is established between the AEs when communication is being carried out therebetween. The association is established in compliance with the ISO/IEEE8650-1 (International Organization for Standardization/Institute of Electrical and Electronic Engineers 8650-1).

Examples of the communication are: (i) notification (without verification) communication utilized in cases where a source AE notifies the content of an ADF to a target AE, (ii) request communication utilized in cases where the source AE acquires information from the target AE, (iii) notification (with verification) communication utilized in cases where the source AE verifies that a data frame has been successfully transmitted to the target AE, (iv) response communication, and (v) check notification communication.

Explained first is the notification (without verification) communication, which is utilized in cases where the source AE notifies the content of an ADF to the target AE. The source AE sets the communication identifier of the AH such that it represents the notification (without verification) communication, and transmits the data frame to the target AE. When the target AE receives the data frame, the target AE carries out error check thereof.

Explained next are the request communication and the response communication.

The request communication is utilized in cases where the source AE acquires information from the target AE. The content of information to be requested is described in the ADF of the data frame to be transmitted from the source AE. The target AE describes the requested information in the ADF of the data frame, and transmits the data frame back to the source AE via the response communication.

Process steps carried out by the source AE in the request communication are as follows:

1) Set the communication identifier of the AH such that it represents the request communication.
2) Set a value in the sequence number of the AH.
3) Set the service identifier of the AH in accordance with the content of a request to the target AE.
4) Describe the content of the request to the target AE in the ADF.
5) Transmit the data frame to the target AE so as to make the request.
6) In cases where any response to the request is not received from the target AE, the source AE may repeatedly transmit thereto the data frame having the same content.
7) When receiving the response communication from the target AE in reply to the request communication, the source AE carries out error check thereof. In cases where there is found no error, the source AE checks the respective values of the sequence number and the service identifier of the AH so as to recognize that the response communication corresponds to what request communication.

Meanwhile, process steps carried out by the target AE in the request communication are as follows:

1) Carry out error check of the data frame upon reception thereof.
2) Check the identifiers of the AH.
3) Carry out a process as requested by the content of the ADF.
4) Set the communication identifier of the AH such that it represents the response communication.
5) Set a value in the sequence number of the AH.
6) Set, in the service identifier, the same value as the value of that in the AH used in the request communication.
7) Set a process result requested by the ADF.
8) Transmit the data frame to the source AE having made the request communication.

The following explains the notification (with verification) communication and the check notification communication.

The notification (with verification) communication is used in cases where the source AE verifies that the data frame has been successfully transmitted to the target AE.

Process steps carried out by the source AE in the notification (with verification) communication are as follows:

1) Set the communication identifier of the AH such that it represents the notification (with verification) communication.
2) Set a value in the sequence number of the AH.
3) Set the service identifier of the AH in accordance with the content of the notification to the target AE.
4) Describe, in the ADF, the content of the notification to the target AE.
5) Transmit the data frame to the target AE via the notification (with verification) communication.
6) In cases where the check notification communication is not received from the target AE in reply to the notification (with verification) communication or where the content of the error check notified via the check notification communication is wrong, the source AE may repeatedly transmit thereto the data frame having the same content.
7) When the check notification communication is received from the target AE in reply to the notification (with verification) communication, the source AE carries out error check thereof. In cases where there is found no error, the source AE checks the respective values of the sequence number and the service identifier of the AH so as to recognize that the check notification communication corresponds to what notification (with verification) communication.

Process steps carried out by the target AE for the notification (with verification) communication are as follows:

1) Carry out error check of the data frame upon reception thereof.
2) Check the identifiers of the AH.
3) Set the communication identifier of the AH such that it represents the check notification communication.
4) Set a value in the sequence number of the AH.
5) Set, in the service identifier, the same value as the value of that in the AH for the notification (with verification) communication.
6) Set the content of the error check in the ADF.
7) Transmit the data frame to the source AE having made the notification (with verification) communication.

[Data Field]

The following explains the data field.

Generally, the ADF is made up of a plurality of continuous data fields. A data field is described in either the single-value data format or the multi-value data format.

The single-value data format is employed for the data communication and the inquiry communication. The multi-value data format is employed for the device registration communication and the communication information registration communication.

Explained first is the single-value data format.

A data field described in the single-value data format is constituted by DL, BN, and DV. Described in the DL is the length of the data field. Described in the BN is a value indicating a communication item. Described in the DV is a data value corresponding to the BN.

Explained next is the multi-value data format.

The data field described in the multi-value data format is constituted by a DL, a DD, a CD, and a DV. Described in the DL is the length of the data field. Described in the DD is a value for identifying each item for either device registration or communication information registration. Described in the CD is a type of text code described in the DV. Described in the DV is a value corresponding to the DD.

Explained next is a data field used for each of the check notification communication and the response communication.

An ADF for the check notification communication is constituted by a V field, which is one data field complying with the single-value data format.

Such a V field is described in the first data field of the ADF for the response communication.

The V field is constituted by a BN and a DV. Set in the V field are as follows:

a value indicating Verification (V) is set in the BN; and a value of the error check identifier is set in the DV.

FIG. 11 illustrates a bit sequence representing data items of the first byte of the DV of the V field.

[Judgment Process]

Explained here is a judgment process for making description in the V field.

When the HCD application receives either the request communication or the notification (with verification) communication from the HMD application, the HCD application checks the device registration status and the communication information registration status of the HMD application having transmitted the request communication or the notification (with verification) communication.

In cases where the description in the ADF is in compliance with the single-value data format, the HCD application checks whether or not the each of the BNs described in the data field is a BN designated by a UDN that the HMD application, which is the transmitting end, has registered in registration communication.

In transmitting the response communication or the check notification communication, the HCD application adds, in the V field of the ADF as a judgment result, (i) a value of the device registration judgment identifier indicating the device registration status, and (ii) a value of the communication information registration judgment identifier indicating the communication information registration status. In cases where there is found an unregistered BN as a result of checking the BN registration status, the unregistered BN is also additionally described in the V field.

In the meanwhile, when the HMD application receives from the HCD application either the request communication or the notification (with verification) communication in compliance with the single-value data format, the HMD application checks whether or not each of the BNs described in the data field is a BN designated by a UDN defined in registration communication.

In cases where there is found an unregistered BN in transmitting either the response communication or the check notification communication, the unregistered BN is additionally described in the V field as a judgment result.

[Device Registration Communication]

The device registration communication is carried out for the purpose of registering, in the HCD application, the HMD's vendor name, product name, model number, UDN, and health measuring device protocol version number. Either one of the product name and the model number may be registered. The device registration communication is communication carried out first between the HMD application and the HCD application. However, at an arbitrary timing after the device registration communication, the device registration communication may be repeated. Further, via the device registration communication, the HMD application can make a request to delete a device registration item registered in the HCD application.

[Device Registration Items]

The device registration items are: the health measuring device protocol version number, the vendor name, the product name, the model number, the UDN, registration deletion. Each of them is described in a data field in the multi-value data format.

It is desirable that all the device registration items be registered by making the device registration communication at one time; however, the device registration items may be registered by making device registration communication for a plurality of times.

It is desirable that the health measuring device protocol version number be described in one data field coming first in the ADF.

The following explains the format of description in the ADF for the device registration communication. Note that the DD has a value indicating that a registration name is described, and the DV has a value indicating a health measuring device protocol version number.

In the case of registering a vendor name, two continuous data fields are described as follows:
the DD of the first data field: a value indicating that a registration name is described;
the DV of the first data field. a character string defining the vendor name;
the DD of the second data field: a value indicating that a name is described;
the DV of the second data field: a character string representing the vendor name.

In the case of registering a product name, two continuous data fields are described as follows:
the DD of the first data field: a value indicating that a registration name is described;
the DV of the first data field: a character string defining the product name;
the DD of the second data field: a value indicating that a name is described; and
the DV of the data field, a character string representing the product name is described.

In the case of registering a model number, two continuous data fields are described as follows:
the DD of the first data field: a value indicating that a registration name is described;
the DV of the first data field DV: a character string defining the model number;
the DD of the second data field: a value indicating that a name is described;
the DV of the second data field: a character string or a code value each representing the model number.

In the case of registering a UDN, two continuous data fields are described as follows:
the DD of the first data field: a value indicating that a registration name is described;
the DV of the first data field: a character string defining the UDN;
the DD of the second data field: a value indicating that a name is described;
the DV of the second data field: a character string representing the UDN.

In the case of carrying out registration deletion, one data field is described as follows:
DD: a value indicating that a registration name is described; and
DV: a character string defining the registration deletion.

[Device Registration Sequence]

The device registration can be carried out from both the HMD application and the HCD application. First, the following explains device registration notification from the HMD application.

Process steps carried out by the HMD application are as follows.

a) Set the communication identifier of the AH such that it represents either the notification (with verification) communication or the notification (without verification) communication.

b) Set a value in the sequence number of the AH.

c) Set the service identifier of the AH such that it represents the device registration communication.

d) Set, in the ADF, a data field in which a device registration item is described.

e) Transmit the data frame to the HCD application.

f) Wait for reception of the check notification communication from the HCD application, in cases where the data frame is for the notification (with verification) communication.

g) When receiving the check notification communication from the HCD application, the HMD application carries out error check thereof. In cases where there is found no error, the HMD application checks the respective values of the sequence number and the service identifier of the AH so as to recognize that the check notification communication corresponds to what notification (with verification) communication.

h) Check the respective values of the error check identifier, the device registration judgment identifier, and the communication information registration judgment identifier in the V field.

Meanwhile, process steps carried out by the HCD application are as follows.

a) Carry out error check, when receiving the data frame from the HMD application.

b) Check the identifiers of the AH.

c) Read out a device registration item from the ADF and carry out a device registration process for the HMD application having transmitted the data frame.

d) Carry out the judgment process.

e) Set the communication identifier of the AH such that it represents the check notification communication, in cases where the communication identifier of the received data frame is set to represent the notification (with verification) communication.

f) Set a value in the sequence number of the AH.

g) Set, in the service identifier, the same value as the value of that in the AH of the received data frame.

h) Set the error check identifier and the judgment process result in the V field.

i) Transmit the data frame to the HMD application having transmitting the data frame.

Explained next is the device registration request from the HCD application.

Process steps carried out by the HCD application are as follows.

a) Set the communication identifier of the AH such that it represents the request communication.

b) Set a value in the sequence number of the AH.

c) Set the service identifier of the AH such that it represents the device registration communication.

d) Describe nothing in the ADF.

e) Transmit the data frame to the HMD application.

f) Wait for reception of a response communication from the HMD application.

g) When receiving the response communication from the HMD application, the HCD application carries out error check thereof. In cases where there is found no error, the HCD application checks the respective values of the sequence number and the service identifier of the AH so as to recognize that the response communication corresponds to what request communication.

h) Check the value of the error check identifier of the V field.

i) Read out a device registration item from the ADF, and carry out a device registration process for the HMD application having transmitted the response communication.

Meanwhile, process steps carried out by the HMD application are as follows.

a) When receiving a data frame from the HCD application, the HMD application carries out error check thereof.

b) Check the identifiers of the AH.

c) Set the communication identifier of the AH such that it represents the response communication.

d) Set a value in the sequence number of the AH.

e) Set, in the service identifier, the same value as the value of that in the AH of the received data frame.

f) Set the value of the error check identifier in the V field.

g) Describe a device registration item in the subsequent data field.

h) Transmit the data frame to the HCD application.

Explained next is device registration verification from the HMD application.

Process steps carried out by the HMD application are as follows.

a) Set the communication identifier of the AH such that it represents the request communication.

b) Set a value in the sequence number of the AH.

c) Set the service identifier of the AH such that it represents the device registration communication.

d) Describe nothing in the ADF.

e) Transmit the data frame to the HCD application.

f) Wait for reception of the response communication from the HCD application.

g) When receiving the response communication from the HCD application, the HMD application carries out error check thereof. In cases where there is found no error, the HMD application checks the respective values of the sequence number and the service identifier of the AH so as to recognize that the response communication corresponds to what request communication.

h) Check device registration status in accordance with the content of the ADF.

Meanwhile, process steps carried out by the HCD application are as follows.

a) When receiving the data frame from the HMD application, the HCD application carries out error check thereof.

b) Check the identifiers of the AH.

c) Set the communication identifier of the AH such that it represents the response communication.

d) Set a value in the sequence number of the AH.

e) Set, in the service identifier, the same value as the value of that in the AH of the received data frame.

f) Carry out judgment process.

g) Set the error check identifier and the judgment process result in the V field.

h) Describe, in the subsequent data field, a device registration item of the HMD application having transmitted the request communication.

i) Transmit the data frame to the HMD application.

The following explains deletion of device registration from the HMD application.

Process steps carried out by the HMD application are as follows.

a) Set the communication identifier of the AH such that it represents either the notification (with verification) communication or the notification (without verification) communication.

b) Set a value in the sequence number of the AH.

c) Set the service identifier of the AH such that it represents the device registration communication.

d) Set, in the ADF as device registration items, a data frame in which the health measuring device protocol version number and the registration deletion are described.

e) Transmit the data frame to the HCD application.

f) In the case of the notification (with verification) communication, the HMD application waits for reception of the check notification communication from the HCD application.

g) When receiving the check notification communication from the HCD application, the HMD application carries out error check thereof. In cases where there is found no error, the HMD application checks the respective values of the sequence number and the service identifier of the AH so as to recognize that the check notification communication corresponds to what notification (with verification) communication.

h) Check the respective values of the error check identifier, the device registration judgment identifier, and the communication information registration judgment identifier in the V field.

Meanwhile, process steps carried out by the HCD application are as follows.

a) When receiving a data frame from the HMD application, the HCD application carries out error check thereof.

b) Check the identifiers of the AH.

c) Read out a device registration item from the ADF, and carry out a device registration deletion process of the HMD application having transmitted the data frame.

d) Carry out judgment process.

e) In cases where the communication identifier of the received data frame is set to indicate the notification (with verification) communication, the HCD application sets the communication identifier of the AH such that it represents the check notification communication.

f) Set a value in the sequence number of the AH.

g) Set, in the service identifier, the same value as the value of that in the AH of the received data frame.

h) Set the error check identifier and the judgment process result in the V field.

i) Transmit the data frame to the HMD application having transmitted the foregoing data frame.

[Communication Information Registration Communication]

The communication information registration communication is carried out for the purpose of registering, in the HCD application, (i) a BN designated by a UDN, (ii) the name of a communication item correlated with the BN, (iii) a unit, and (iv) a scale.

The communication information registration communication may be repeated to add or change a BN to be registered. In the communication information registration communication, the HCD application recognizes, in accordance with a UDN described in an ADF, a collection of BNs to be registered, and adds or changes BNs. By designating a UDN, the HMD application can make reference to a communication item registered in the HCD application.

The following first explains the structure of the ADF for the communication information registration.

Data fields in the structure of the ADF for the communication information registration are described in the multi-value data format. Note that the ADF for the communication information registration is made up of a UDN field and communication information fields. In the following, a DL and a CD therein are omitted.

The UDN field is structured as follows.

DD: a value indicating that the UDN is described.
DV: a character string representing the UDN.

In cases where the communication method is the notification (with verification) communication, the notification (without verification) communication, or the request communication and where the UDN field is described, the UDN field must be described first in the data frame. In cases where the communication method is the response communication, the UDN field is described in a data field coming just after the V field.

The communication information field is made up of a plurality of continuous data fields. The first data field of the data fields designates a BN, and data fields coming after the first data field designate a name, a unit, and a scale.

A plurality of data fields may be used to designate names. The data fields designating the unit and the scale may be omitted.

The communication information field is structured as follows. Note that a DL and a CD therein are omitted.

DD: a value indicating that a registration name is described
DV: the value of the BN
DD: a value indicating that a name is described
DV: the name 1 of a communication item
DD: a value indicating that a name is described
DV: the name 2 of a communication item
... (Repeated as required) ...
DD: a value indicating that a unit is described
DV: a character string representing a unit
DD: a value indicating that a scale is described
DV: a character string representing a scale In the case where a plurality of communication items are to be registered, a plurality of continuous communication information fields are used.

[Communication Information Registration Sequence]

The following explains a communication information registration sequence.

A case of the communication information registration notification from the HMD application will be described.

Process steps carried out by the HMD application are as follows.

a) Set the communication identifier of the AH such that it represents the notification (with verification) communication or the notification (without verification) communication.

b) Set a value in the sequence number of the AH.

c) Set the service identifier of the AH to indicate the communication information registration communication.

d) Describe the UDN field in the first data field of the ADF. Describe a character string representing the UDN registered in the device registration communication.

e) Set, in the ADF, a data field in which a communication information registration item is described.

f) Transmit the data frame to the HCD application.

g) Wait for reception of the check notification communication from the HCD application, in the case of the notification (with verification) communication.

h) When receiving the check notification communication from the HCD application, the HMD application carries out error check thereof. In cases where there is found no error, the HMD application checks the sequence number and the service identifier of the AH, and recognizes that the check notification communication corresponds to what notification (with verification) communication.

i) Check the respective values of the error check identifier, the device registration judgment identifier, and the communication information registration judgment identifier in the V field.

Meanwhile, process steps carried out by the HCD application are as follows:

a) When receiving the data frame from the HMD application, the HCD application carries out error check thereof.

b) Check the identifiers of the AH.

c) Read out the communication information registration item from the ADF, and carry out communication information registration process for the HMD application having transmitted the data frame.

d) Carry out judgment process.

e) In cases where the communication identifier of the received data frame is set to indicate the notification (with verification) communication, the HCD application sets the communication identifier of the AH such that it represents the check notification communication.

f) Set a value in the sequence number of the AH.

g) Set, in the service identifier, the same value as the value of that in the AH of the received data frame.

h) Set the error check identifier and the judgment process result in the V field.

i) Transmit the data frame to the HMD application having transmitted the foregoing data frame.

A case of the communication information registration request from the HMD application will be described.

Process steps carried out by the HMD application are as follows.

a) Set the communication identifier of the AH such that it represents the request communication.

b) Set a value in the sequence number of the AH.

c) Set the service identifier of the AH such that it represents the communication information registration communication.

d) Describe the UDN field in the ADF, and describe, in the DV, a character string defining the UDN to be referred. In cases where the HMD application makes reference to a communication item of the HMD application registered in the HCD application and having transmitted foregoing data frame, description in the UDN field may be omitted and nothing may be described in the ADF.

e) Transmit the data frame to the HCD application.

f) Wait for reception of the response communication from the HCD application.

g) When receiving the response communication from the HCD application, the HMD application carries out error check thereof. In cases where there is found no error, the HMD application checks the respective values of the sequence number and the service identifier of the AH, and recognizes that the response communication corresponds to what request communication.

h) Check registration status of the communication item of the designated UDN in accordance with the content of the ADF.

Meanwhile, process steps carried out by the HCD application are as follows.

a) When receiving the data frame from the HMD application, the HCD application carries out error check thereof.

b) Check the identifiers of the AH.

c) Read out the UDN described in the UDN field of the ADF.

d) Prepare, as a communication information field, all the communication items registered via the readout UDN.

e) In cases where nothing is described in the ADF, the HCD application prepares, as a communication information field, all the communication items registered via the UDN that the HMD application has registered in the device registration communication.

f) Set the communication identifier of the AH such that it represents the response communication.

g) Set a value in the sequence number of the AH.

h) Set, in the service identifier, the same value as the value of that in the AH of the received data frame.

i) Carry out a judgment process.

j) Set the error check identifier and the judgment process result in the V field coming first in the ADF.

k) Set, in the subsequent data field, the same UDN field as that of the received data frame.

l) Set, in the subsequent data field, the prepared communication information field.

m) Transmit the data frame to the HCD application.

A case of a communication information registration request from the HCD application will be described.

Process steps carried out by the HCD application are as follows.

a) Set the communication identifier of the AH such that it represents the request communication.

b) Set a value in the sequence number of the AH.

c) Set the service identifier of the AH such that it represents the communication information registration communication.

d) Describe nothing in the ADF.

e) Transmit the data frame to the HMD application.

f) Wait for reception of the response communication from the HMD application.

g) When receiving the response communication from the HMD application, the HCD application carries out error check thereof. In cases where there is found no error, the HCD application checks the respective values of the sequence number and the service identifiers of the AH, and recognizes that the response communication corresponds to what request communication.

h) Check the value of the error check identifier in the V field.

i) Read the communication information registration item from the ADF, the HCD application carries out a communication information registration process for the HMD application having transmitted the foregoing data frame.

Meanwhile, process steps carried out by the HMD application are as follows.

a) When receiving the data frame from the HCD application, the HMD carries out error check thereof.

b) Check the identifiers of the AH.

c) Set the communication identifier of the AH in the response communication.

d) Set a value in the sequence number of the AH.

e) Set, in the service identifier, the same value as the value of that in the AH of the received data frame.

f) Set the value of the error check identifier in the V field coming first in the ADF.

g) Describe the UDN field in the subsequent data field. Describe a character string representing the UDN registered upon the device registration communication.

h) Describe the communication information field in the field coming just after the UDN field.

i) Transmit the data frame to the HCD application.

[Data Communication]

The data communication is carried out such that the HMD application sends data to the HCD application.

A BN to be used should be a component of a collection of BNs designated by a UDN registered in the HCD application upon the device registration communication.

The following explains the structure of the ADF in the data communication.

Data fields used in the data communication are described in the single-value data format.

Health information of a person is described in a health information field.

Health information field:

BN: the value of a BN corresponding to a personal ID

DV: the value of the personal ID

BN: the value of a BN corresponding to measurement time

DV: the value of measurement time

BN: the value of a BN corresponding to a measurement item 1

DV: the value of the measurement item 1

BN: the value of a BN corresponding to the measurement item 2

DV: the value of the measurement item 2

... (Repeated as required) ...

It is desired that the personal ID be described in the first data field in the health information field.

In the data field coming after the first data field, measurement time is described. After the data field, there are provided a plurality of data fields in which measurement items are described.

The data field indicating the measurement time may be omitted.

A plurality of health information fields may be described in one ADF.

[Data Communication Sequence]

Explained next is data communication sequence.

Now, a case of data communication notification from the HMD application will be described.

In this case, process steps carried out by the HMD application are as follows.

a) Set the communication identifier of the AH such that it represents the notification (with verification) communication or the notification (without verification) communication.

b) Set a value in the sequence number of the AH.

c) Set the service identifier of the AH to indicate the data communication.

d) Set a data communication item in the ADF.

e) Transmit the data frame to the HCD application.

f) In the case of the notification (with verification) communication, the HMD application waits for reception of the check notification communication from the HCD application.

g) When receiving the check notification communication from the HCD application, the HMD application carries out error check thereof. In cases where there is found no error, the HMD application checks the respective values of the sequence number and the service identifier of the AH so as to recognize that the check notification communication corresponds to what notification (with verification) communication.

h) Check the respective values of the error check identifier, the device registration judgment identifier, the communication information registration judgment identifier, in the V field.

Process steps carried out by the HCD application are as follows.

a) When receiving the data frame from the HMD application, the HCD application carries out error check thereof.

b) Check the identifiers of the AH.

c) Read out the ADF, and carry out a process of data communication.

d) Carry out a judgment process.

e) In cases where the communication identifier of the received data frame is set to indicate the notification (with verification) communication, the HCD application sets the communication identifier of the AH such that it represents the check notification communication.

f) Set a value in the sequence number of the AH.

g) Set, in the service identifier, the same value as the value of that in the AH of the received data frame.

h) Set the error check identifier and the judgment process result in the V field.

i) Transmit the data frame to the HMD application.

Now, a case of data communication request from the HCD application will be described.

In this case, process steps carried out by the HCD application are as follows.

a) Set the communication identifier of the AH such that it represents the request communication.

b) Set a value in the sequence number of the AH.

c) Set the service identifier of the AH such that it represents the data communication.

d) Describe nothing in the ADF.

e) Transmit the data frame to the HMD application.

f) Wait for reception of the response communication from the HMD application.

g) When receiving the response communication from the HMD application, the HCD application carries out error check thereof. In cases where there is found no error, the HCD application checks the respective values of the sequence number and the service identifier of the AH and recognizes that the response communication corresponds to what request communication.

h) Check the value of the error check identifier in the V field.

i) Read out the ADF and carry out a predetermined process.

Meanwhile, process steps carried out by the HMD application are as follows.

a) When receiving the data frame from the HCD application, the HMD application carries out error check thereof.

b) Check the identifiers of the AH.

c) Set the communication identifier of the AH such that it represents the response communication.

d) Set a value in the sequence number of the AH.

e) Set, in the service identifier, the same value as the value of that in the AH of the received data frame.

f) Set the value of the error check identifier in the V field coming first in the ADF.

g) Set a data communication item in the subsequent data field.

h) Transmit the data frame to the HCD application.

[Inquiry Communication]

The inquiry communication is made by the HMD application so as to inquire information from the HCD application. Further, via the inquiry communication, the HCD application can notify predetermined information to the HMD application.

The following explains the structure of the ADF for the inquiry communication.

A data field for the inquiry communication is described in the single-value data format.

The HMD application describes, in an inquiry field, a BN corresponding to information to be inquired.

The inquiry field is structured as follows.

BN: the value of a BN corresponding to measurement time.

DV: the value of the measurement time.

BN: the value of a BN corresponding to information to be inquired.

DV: nothing described.

In the inquiry field, a data field designating the measurement time may be provided.

In this case, the HCD application retrieves information corresponding to a measurement time closest to the designated measurement time, among inquired information corresponding to measurement times coming before the designated measurement time.

For inquiring information regarding a person's health information, the personal ID is designated in a health information field and a data field for the information to be inquired is described as the inquiry field.

The HMD application may describe a UDN field in an arbitrary position in the ADF. In this case, each of BN values of data fields until the next UDN field is set at the value of the BN designated by the UDN described in the UDN field.

For data fields for the response communication to be carried out by the HCD application, the data fields for the request communication are reused apart from the V field. Further, in the data fields, a value is additionally described in the DV of the inquiry field. In cases where a data field designating the measurement time exists in the inquiry field, the value of the DV is replaced with the value of the measurement time of the retrieved information.

In cases where the HCD application make communication so as to give a notification, the HMD application describes the data fields with the use of the component of the collection of BNs designated by the UDN registered upon the device registration communication.

[Inquiry Communication Sequence]

The following explains an inquiry communication sequence.

A case of an inquiry request from the HMD application will be described.

In this case, process steps carried out by the HMD application are as follows.

a) Set the communication identifier of the AH such that it represents the request communication.
b) Set a value in the sequence number of the AH.
c) Set the service identifier of the AH such that it represents the inquiry communication.
d) Describe an inquiry communication item in the ADF.
e) Transmit the data frame to the HCD application.
f) Wait for reception of the response communication from the HCD application.
g) When receiving the response communication from the HCD application, the HMD application carries out error check thereof. In cases where there is found no error, the HMD application checks the respective values of the sequence number and the service identifier of the AH so as to recognize that the response communication corresponds to what request communication.
h) Check the content of the ADF.

Meanwhile, process steps carried out by the HCD application are as follows.

a) When receiving the data frame from the HMD application, the HCD application carries out error check thereof.
b) Check the identifiers of the AH.
c) Read out the ADF and check the inquiry field.
d) In cases where the inquiry field designates a measurement time, the HCD application retrieves information corresponding to a measurement time closest to the designated measurement time, among inquired information corresponding to measurement times coming before the designated measurement time. In cases where no measurement time is designated, the newest value is retrieved.
e) Set the communication identifier of the AH such that it represents the response communication.
f) Set a value in the sequence number of the AH.
g) Set, in the service identifier, the same value as the value of that in the AH of the received data frame.
h) Carry out a judgment process.
i) Set the error check identifier and the judgment process result in the V field coming first in the ADF.
j) Set a predetermined data field in the subsequent data field.
k) Transmit the data frame to the HMD application.

Now, a case of an inquiry notification from the HCD application will be described.

Process steps carried out by the HCD application are as follows.

a) Set the communication identifier of the AH such that it represents the notification (with verification) communication or the notification (without verification) communication.
b) Set a value in the sequence number of the AH.
c) Set the service identifier of the AH such that it represents the inquiry communication.
d) Set, in the ADF, data fields with the use of the BNs designated by the UDN registered by the HMD application upon the device registration communication.
e) Transmit the data frame to the HMD application.
f) In the case of the notification (with verification) communication, the HCD application waits for reception of the check notification communication from the HMD application.
g) When receiving the check notification communication from the HMD application, the HCD application carries out error check thereof. In cases where there is found no error, the HCD application checks the respective values of the sequence number and the service identifier of the AH so as to recognize that the check notification communication corresponds to what notification (with verification) communication.
h) Check the value of the error check identifier in the V field.

Meanwhile, process steps carried out by the HMD application are as follows.

a) When receiving the data frame from the HCD application, the HMD application carries out error check thereof.
b) Check the identifiers of the AH.
c) Read out the ADF so as to acquire the notified information from the data fields.
d) Carry out a judgment process.
e) In cases where the communication identifier of the received data frame is set to indicate the notification (with verification) communication, the HMD application sets the communication identifier of the AH such that it represents the check notification communication.
f) Set a value in the sequence number of the AH.
g) Set, in the service identifier, the same value as the value of that in the AH of the received data frame.
h) Set the error check identifier and the judgment process result in the V field.
i) Transmit the data frame to the HCD application

[General Operation]

The HMD application provided in the health measuring device first notifies its manufacturer's name, its production number, and the like, to the HCD application, thereby carrying out the device registration. Next, the HMD application notifies thereto health information to be measured, thereby carrying out the communication information registration. Thereafter, the HMD application transmits measured health information to the HCD application together with a code value. As required, the HMD application inquires information held by the HCD application, such as current time and examinee information. Examples of the examinee information include age, sex, and the like.

Note that the HMD application is executed by the control section 206 and the measurement data generating section 202. The storage section 207 stores (i) information regarding the device registration communication and the communication information registration communication, (ii) a current time, (iii) the examinee information, and (iv) measurement values measured by the measuring section 203.

Meanwhile, the HCD application is executed by the control section 107 and the measurement data converting section 104. The code storage section 101 stores (i) the content of the communication information registration communication received from the HMD application, and (ii) a BN allocation table and the communication information registration information each received from the external server 300. The measurement data received from the HMD application is converted by the measurement data converting section 104 with reference to the code storage section 101, and is then stored in the health condition storage section 102. Note that the HCD application identifies, in accordance with the UDN used in the device registration, communication information corresponding to BNs in the measurement data. In the description herein, the UDN used in the device registration is identified and specified from the health measuring device's address, etc., used in a lower layer.

[Example of Description in ADF for Device Registration Communication]

The following explains an example of description in the ADF for the device registration communication.

Data field in cases where the health measuring device protocol version number is "NedohhcVersion 1.1"
DL: 0x00, 0x15
DD: 0x01: a value indicating that a registration name is described
CD: 0x10: ascii code
DV: "NedohhcVersion 1.1"
Data field in cases where the vendor name is "sharp"
First data field:
DL: 0x00, 0x0f
DD: 0x01: a value indicating that a registration name is described
CD: 0x10:ascii code
DV: "Manufacture"
Second data field:
DL: 0x00, 0x09
DD: 0x02: a value indicating that a name is described
CD: 0x10: ascii code
DV: "sharp"
Data field in cases where the product name is "rhythm-kei"
First data field:
DL: 0x00, 0x0d
DD: 0x01: a value indicating that a registration name is described
CD: 0x10: ascii code
DV: "ModelName"
Second data field:
DL: 0x00, 0x0e
DD: 0x02: a value indicating that a name is described
CD: 0x10: ascii code
DV: "rhythm-kei"
Data field in cases where the model number is "01234567"
First data field:
DL: 0x00, 0x0f
DD: 0x01: a value indicating that a registration name is described
CD: 0x10: ascii code
DV: "ModelNumber"
Second data field:
DL: 0x00, 0x0c
DD: 0x02: a value indicating that a name is described
CD: 0x10: ascii code
DV: "01234567"
Data field in cases where UDN is "nedo-zerocrosscount"
First data field:
DL: 0x00, 0x07
DD: 0x01: a value indicating that a registration name is described
CD: 0x10: ascii code
DV: "UDN"
Second data field:
DL: 0X00, 0x17
DD: 0x02: a value indicating that a name is described
CD: 0x10: ascii code
DV: "nedo-zerocrosscount"
Data field in cases where FriendlyMachineName, i.e., device simple name is "motio"
First data field:
DL: 0x00, 0x17
DD: 0x01: a value indicating that a registration name is described
CD: 0x10: ascii code
DV: "FriendlyMachineName"
Second data field:
DL: 0x00, 0x09
DD: 0x02: a value indicating that a name is described
CD: 0x10: ascii code
DV: "motio"
Data field in cases where device registration deletion is carried out
First data field
DL: 0x10, 0x15
DD: 0x01: a value indicating that a registration name is described
CD: 0x10: ascii code
DV: "NedohhcVersion 1.1"
Second data field
DL: 0x00, 0x0e
DD: 0x01: a value indicating that a registration name is described
CD: 0x10: ascii code
DV: "Deregister"

[Example of Description in ADF for Communication Information Registration Communication]

The following describes an example of description in the ADF for the communication information registration communication.

UDN field in cases where the UDN is "nedo-zerocrosscount"
DL: 0x00, 0x17
DD: 0x05: a value indicating that a UDN is described
CD: 0x10: ascii code
DV: "nedo-zerocrosscount"
A communication information field in cases where a communication item whose English name is "calorie", whose Japanese name is a Japanese word corresponding to "calorie", whose unit is "kcal", and whose scale is "0.1" is correlated with a BN "0xb2".
(Note: in this reference example, as described below, one value to be measured is correlated with one BN, and the BN defines several attributes of the value to be measured.)
First data field:
DL: 0x00, 0x05
DD: 0x01: a value indicating that a registration name is described
CD: 0x01: binary code
DV: 0xb2: BN Second data field:
DL: 0x00, 0x0b
DD: 0x02: a value indicating that a name is described
CD: 0x10: ascii code
DV: "calorie"
Third data field:
DL: 0x00, 0x10
DD: 0x02: a value indicating that a name is described
CD: 0x20: JIS code
DV: "Japanese word corresponding to calorie"

Fourth data field:
DL: 0x00, 0x08
DD: 0x03: a value indicating that a unit is described
CD: 0x10: ascii code
DV: "Kcal"
Fifth data field:
DL: 0x00, 0x07
DD: 0x04: a value indicating that a scale is described
CD: 0x10: ascii code
DV: "0.1"

In the DD of the first data field, the value indicating that the registration name is described should be designated; however, the order from the second to fifth data fields is arbitrary.

A unit for a communication item is registered by designating International System of Units (SI) via an ascii code. In cases where a communication item does not have a unit, the registration for a unit is omitted. Further, in cases where a communication item has a scale of 1, registration for the scale may be omitted.

In cases where measurement items such as a measurement time and a current time are to be registered, units are registered by using descriptions of character strings "yy", "MM", "dd", "hh", "mm", and "ss" in DV as follows:
DL: 0x00, 0x0e
DD: 0x03: a value indicating that a unit is described
CD: 0x10: ascii code
DV: "yyMMddhhmmss"

These character strings indicate as follows:
"yy": last two digits of year in western calendar
"MM": month
"dd": date
"hh": hour
"mm": minute
"ss": second A one-byte binary value is described in each of them. In the case of registering a measurement item regarding date and hour, the character strings "yyMMdd" cannot be omitted but the character strings "hh", "mm", and "ss" can be omitted.

An arbitrary character string may be used for the English name of communication information to be registered, as long as the initial letter thereof is a small letter. A character string starting with a capital letter cannot be used for the English name, apart from a standard name.

[Communication Information Field]

With reference to FIG. 9 and FIG. 10, the following explains the communication information field.

PersonalID is described to identify an examinee in the data communication or the like.

MeasurementTime indicates the measurement time of a measurement value, for the data communication or the like.

CurrentTime indicates a current time, is inquired from the HMD application to the HCD application via the inquiry communication, and can be notified from the HCD application.

AllUDN indicates all the UNDs registered in the HCD application. Described in the DV of the AllUDN is a UDN designating a DD with 0x05 and described in the multi byte format. For example, in cases where two UDNs "abcd" and "xyz" are registered therein, the DV is as follows: (DL=0x00, 0x08) (DD=0x05) (CD=0x10) (DV="abcd") (DL=0x00, 0x07) (DD=0x05) (CD=0x10) (DV="xyz").

SelfDiagnosis describes a result of the HMD application's diagnosis on its operation status. In cases where the operation status of the HMD application is normal, the SelfDiagnosis indicates "normal". In cases where the operation status is not normal, the SelfDiagnosis indicates "trouble".

OperatingCondition is used to notify the HMD's operation condition to the HCD application, and is used for judgment as to whether the HMD can respond to an inquiry from the HCD application. For example, when the HMD is brought into a sleep state, the HMD notifies the HCD application that the HMD is in the sleep state, via the OperatingCondition indicating "sleep". With this, the HCD application does not need to carry out unnecessary communication thereafter. Note that while the HMD is operating, the OperatingCondition describes "running". When the HMD is operating intermittently, it describes "intermittent". When the HDM is in the sleep state, it describes "sleep".

BatteryCharge indicates a battery charging rate.

BatteryLife indicates an estimated time at which the battery runs out.

NetworkFailure is used to notify the health measuring device of a communication condition of communication carried out between the HCD application and the server via another communication line. In cases where there is a trouble in the communication, the NetworkFailure indicates "trouble". In cases where there is no trouble therein, the NetworkFailure indicates "normal".

GwServerError is used to notify the HMD application of an error having occurred in communication in which the HCD application transmits, to the server via another communication line, data received from HMD application. Description of a DV is made based on, as a unit, (i) a time at which the HCD application receives from the HMD application data corresponding to the error and (ii) an ADF of the received data. In cases where there are a plurality of errors, descriptions are repeatedly made in the DV based on this unit. The time at which the data is received is described in such a manner as yyMMddhhmmss.

ServerRegister is used by the HCD application to notify the HMD application of whether or not the HMD application has been registered, via another communication line by which the HCD application transmit to the server data received from the HMD application, in the server having a function of registering therein an HMD application. In cases where the HMD application has been registered therein, the ServerRegister describes "reg". In cases where the HMD application has not been registered therein, the ServerRegister describes "unreg".

Advice indicates an advice to the examinee.
Ask-a-doc indicates a question from the examinee.
Sos indicates an emergency report.
FriendlyUserName is a simple name for the examinee.
Age indicates an age.
BirthDate indicates a date of birth.
Sex indicates a sex. In cases where the examinee is a male, Sex describes "male", and in cases where the examinee is a female, Sex describes "female".
BodyHeight indicates a height.
BodyTemp indicates a body temperature.
UrineSugar indicate a urine sugar value.
SysBP indicates a maximum blood pressure.
DiasBP indicates a minimum blood pressure.
MeanBP indicates an average blood pressure.
HeartRate indicates a heart rate.
BodyWeight indicates a body weight.
BodyFat indicates a body fat percentage.
BloodGlucose indicates a blood glucose level.

[Example of Description of ADF for Data Communication]

The following explains an example of description of an ADF for the data communication.

Health information field in cases where communication information registration is made with the personal ID designated by a BN "0x20", the measurement time designated by a BN "0x10", the weight designated by a BN "0x03", and the blood pressure designated by a BN "0x04":

(DL, 0x20, DV=personal ID) (DL, 0x10, DV=measurement time) (DL, 0x03, DV=weight) (DL, 0x04, DV=blood pressure)

In each data field, the DV is described based on the unit and scale utilized in the communication information registration.

In the data field coming first in the ADF, it is possible to describe a UDN. In this case, the BN is set to be 0x01 and the UDN is described in the DV thereof.

Data fields of an ADF in the case of making the communication information registration with the personal ID designated by a BN "0x20", the measurement time designated by a BN "0x10", the body weight designated by a BN "0x03", and the blood pressure designated by a BN "0x04": (DL, 0x01, DV=UDN) (DL, 0x20, DV=personal ID) (DL, 0x10, DV=measurement time) (DL, 0x03, DV=body weight) (DL, 0x04, DV=blood pressure)

In cases where the data for the communication is not the health information regarding the examinee, an order of description of the data fields are not particularly designated apart from the UDN, which should be described in the data field coming first in the ADF.

The following explains an example of description of an ADF for the inquiry communication.

Inquiry field in cases where the HMD application acquires a current time from the HCD application in which the current time is registered with a BN "0x30", and a unit "yyMMddhhmm":
(Current time)
(0x00, 0x03, 0x30)

Inquiry field replying from the HCD application for the current time
(current time: 18:10, February 17, 04)
(0x00, 0x08, 0x30, 0x040211120a)

Inquiry field and health information field for acquiring (i) the current time, (ii) the age of an examinee rendered a personal ID No. 1, and (iii) the body weight of an examinee rendered a personal ID No. 2, from the HCD application in which the HMD application has registered the current time with a BN "0x30" and the unit "yyMMddhhmm" and has registered the personal ID with a BN "0x20", the age with a BN "0x0a", and the body weight with a BN "0x0b":
(current time) (personal ID: No. 1) (age) (personal ID: No. 2) (body weight)
(0x00, 0x03, 0x30) (0x00, 0x04, 0x20, 0x01) (0x00, 0x03, 0x0a) (0x00, 0x04, 0x20, 0x02) (0x00, 0x03, 0x0b)

Inquiry field and health information field used in cases where the HCD application notifies the current time, the age of the examinee rendered the personal ID No. 1, and the body weight of the examinee rendered the personal ID No. 2, in reply:
(Note that: in this example, one BN is correlated with one measurement value. The wording "measurement value" herein is not limited to a narrowly-defined measurement value, i.e., a value actually measured by a measuring device, but encompasses broadly-defined measurement value, i.e., information inputted through an input operation, such as an age.)
(Current time: 18:10, February 17, 04) (personal ID No. 1) (age: 23) (personal ID: No. 2) (body weight: 60 kg)
(0x0, 0x08, 0x30, 0x040211120a) (0x00, 0x04, 0x20, 0x01) (0x00, 0x04, 0x0a, 0x17) (0x00, 0x04, 0x20, 0x02) (0x00, 0x0d, 0x0b, 0x3c)

Inquiry field and health information field for acquiring data indicating the blood pressure of the examinee of the personal ID No. 1 and corresponding to a measurement time "18:15, February 17, 04", from the HCD application, in cases where the HMD application has registered therein the measurement time with a BN "0x40", the unit with "yyMMddhhmm", the personal ID with a BN "0x20", and the blood pressure with a "BN:0x0c":
(personal ID: No. 1) (measurement time: 18:15, February 17, 04) (blood pressure)
(0x00, 0x04, 0x20, 0x01) (0x00, 0x05, 0x40, 0x040211120f) (0x00, 0x03, 0x0c)

In cases where a measurement time coming before and closest to the designated measurement time is 18:10, February 17, 04, the HCD application describes the measurement time and the blood pressure of the examinee of the personal ID No. 1 as follows for response.
(personal ID: No. 1) (measurement time: 18:10, February 17, 04) (blood pressure 125 mmHg)
(0x00, 0x04, 0x20, 0x01) (0x00, 0x08, 0x40, 0x040211120a) (0x00, 0x04, 0x0c, 0x7d)

Inquiry field and health information field for making a reference to data of the body weight of an examinee of the personal ID No. 1 in a target device that (i) has an HMD application having registered the personal ID with a BN "0x20", (ii) is registered with a UDN "abed" in which measurement time is registered with a BN "0xd1" and weight is registered with a BN "0xd2", and (iii) has measured the body weight on 18:16, February 17, 04:
(personal ID: No. 1) (UDN "abcd") (measurement time: 18:16, Feburary 17, 04) (body weight)
(0x00, 0x04, 0x20, 0x01) (0x00, 0x7, 0x01, 0x61, 0x62, 0x63, 0x64) (0x00, 0x08, 0xd1, 0x0402111210) (0x00, 0x04, 0xd2)

In cases where measurement time coming before and closest to the designated measurement time is 18:15, February 17, 04, the HCD application describes, for response, the body weight of the examinee of the personal ID No. 1, which body weight has been measured at the measurement time by the device whose UDN is "abcd", as follows:
(personal ID: No. 1) (UDN "abcd") (measurement time: 18:15, Feburary 17, 04) (body weight: 60 kg)
(0x00, 0x04, 0x20, 0x01) (0x00, 0x7, 0x01, 0x61, 0x62, 0x63, 0x64) (0x00, 0x08, 0xd1, 0x040211120f) (0x00, 0x04, 0xd2, 0x3c)<

Embodiment

In the information acquiring device and the measurement data communication device according to Reference Example above, one BN is correlated with one measurement value, and one BN cannot be correlated with a plurality of measurement values. Further, it is impossible for the information acquiring device to request the measurement data communication device for an operation condition, a measurement condition, a vital parameter, and the like. Further, it is impossible that the information acquiring device sets an operation condition, data, and the like in the measurement data communication device or the measurement data communication device sets them in the information acquiring device. Further, it is impossible to designate a data type of data format and utilize a description using XML.

In contrast, a structure of the present embodiment allows a plurality of measurement values to be correlated with a BN, allows an information acquiring device to request a measurement data communication device for an operation condition, a measurement condition, and a vital parameter, allows the information acquiring device to set an operation condition and data in a measurement data communication device or allows a measurement data communication device to set an operation condition and data in the information acquiring device, and allows designation of a data type of a data format and use of a description using XML.

The following explains an information acquiring device and a measurement data communication device each having such a structure. In the present embodiment, only differences from Reference Example will be described.

[Correlating a BN with a Plurality of Measurement Values]

In Reference Example, the standard names for registering one communication information via the communication information registration communication are illustrated in FIG. 9, whereas communication information registration communication in the present embodiment utilizes a code space defined by ISO/IEEE11073-10101 Nomenclature. The code space defines a relation between a healthcare-related target object and a code, so that it is possible to identify each waveform of an electrocardiogram.

The following explains communication information registration communication carried out in cases where a health measuring device application measures a plurality of measurement values and allocate one BN to the plurality of measurement values. FIG. 12 illustrates extensions of reserved words used in this case.

A communication information field in this case is as follows. The communication information field herein corresponds to the communication information field used for the communication information registration communication in Reference Example. A difference therebetween lies in that: while one BN is correlated with one measurement value in the communication information field described in Reference Example, one BN is correlated with a plurality of measurement values, such as the first measurement value and the second measurement value, in this example.

Note that, in the example below, DLs are not described.
DD: a value indicating that a registration name is described (0x01)
CD: binary code (0x01)
DV: the value of a BN
==Registration of the first measurement value==
DD: a value indicating that a registration name is described
CD: ascii
DV: "MetricSpecification"
DD: a value indicating MetricValue is described
CD: Nomenclature code (0x02)
DV: Metric's code value of the first measurement value in Nomenclature
DD: A value indicating that a registration name is described
CD: ascii
DV: "MetricLocation"
DD: a value indicating that MetricValue is described
CD: INT-U16 (0x03)
DV: a location in which the measurement value appears
DD: a value indicating that a data type is described (0x06)
CD: Nomenclature code (0x02)
DV: Nomenclature code value indicating a data type of the first measurement value
DD: a value indicating that a name is described
CD: the value of a code identifier indicating a code described in the subsequent DV
DV: the name 1 of a communication item of the first measurement value
DD: a value indicating that a name is described
CD: the value of a code identifier indicating a code described in the subsequent DV
DV: the name 2 of a communication item of the first measurement value
. . . (Repeated as required) . . .
DD: a value indicating that a unit is described
CD: the value of a code identifier indicating a code described in the subsequent DV
DV: a character string indicating a unit for the first measurement value
==Registration of the second measurement value==
DD: a value indicating a registration name is described
CD: ascii
DV: "MetricSpecification"
DD: a value indicating that MetricValue is described
CD: Nomenclature code (0x02)
DV: a code value of Metric of Nomenclature of the second measurement value
DD: a value indicating that a registration name is described
CD: ascii
DV: "MetricLocation"
DD: a value indicating that MetricValue is described
CD: INT-U16 (0x03)
DV: a location in which the second measurement value appears
DD: a value indicating that a data type is described (0x06)
CD: ascii code (0x10)
DV: "XML"
DD: a value indicating that a name is described
CD: the value of a code identifier indicating a code described in the subsequent DV
DV: the name 1 of a communication item of the second measurement value
DD: a value indicating that a name is described
CD: the value of a code identifier indicating a code described in the subsequent DV
DV: the name 2 of a communication item of the second measurement value
. . . (Repeated as required) . . .
DD: a value indicating that a unit is described
CD: a value of a code identifier indicating a code described in the subsequent DV
DV: a character string indicating a unit for the measurement value
. . . (the same as above) . . .
==Registration of the n-th measurement value==
. . . (the same as above) . . .

The above is the example of the communication information field.

The respective data fields of the above communication information field will be explained below one by one. Note that this data frame has an AH in which a service identifier is designated to indicate "communication information registration".

In the first data field, the DD represents the value indicating that the registration name is described and the CD represents the binary code so as to designate the BN code allocated to attributions defined in the following data fields.

In the following data field, the DD represents the value indicating that the registration name is described, the CD represents the ascii, the DV is "MetricSpecification", which is an extension shown in FIG. 12 and is a character string indicating a type of measurement value, thereby indicating that the type of measurement value is designated in the subsequent data field.

In the subsequent data field, the DD represents the value indicating that MetricValue is described and the CD represents the Nomenclature code (0x02), so as to indicate the type of measurement value by using the code space defined by the ISO/IEEE 11073-10101 Nomenclature. Designated in the DV is the code corresponding to the relevant measurement value and defined in the ISO/IEEE11073-10101 Nomenclature.

In the subsequent data field, the DD represents a value indicating that a registration name is described, the CD represents the ascii, and the DV represents "MetricLocation", which is an extension shown in FIG. 12 and is a character string indicating a type of measurement value, thereby indicating that the subsequent data field designates, in accordance with the number of bytes from the first one, where in the ADF the measurement value appears.

In the subsequent data field, the DD represents a value indicating that MetricValue is described, and the CD represents the INT-U16 code (0x03), thereby indicating, with the use of the INT-U16, that where in the ADF the measurement value appears is to be designated. The DV designates, by using the INT-U16, where in the ADF the measurement value appears.

In the subsequent data field, the DD represents a value indicating that the data type is described (0x06), and the CD represents the Nomenclature code (0x02), thereby indicating, with the use of the code space defined by the ISO/IEEE11073-10101 Nomenclature, that the data type is to be designated. The DV designates the code corresponding to the relevant data type and defined by the ISO/IEEE11073-10101 Nomenclature.

In the data fields thereafter, the name and unit (or names and units) are designated.

As described above, after the communication information of the first measurement value, the respective communication information of the second and third measurement values are described. In this way, a plurality of measurement values are correlated with one BN.

Namely, the first measurement value and the second measurement value are correlated with one BN by (i) defining the number of a new BN in the first data field, (ii) defining registration of the first measurement value in the subsequent data field, (iii) setting, in the DD of the subsequent data field, the value (0x01) indicating that the registration name is described, setting the ascii (0x10) in the CD, and setting "MetricSpecification" in the DV as shown in the example.

With the settings, the designation, defined in the subsequent data field, of the type of measurement value and the measurement value defined by the designation are correlated with the same BN.

The definition for registration of the third measurement value can be made by making the same description, thus being correlated with the same BN.

In cases where a different BN is defined just after finishing defining the attributions of the plurality of measurement values for one BN, the DD of the next data field is set at a value indicating that a registration name is described, the CD thereof is set at a value indicating that a binary code is described, and the DV thereof is set with a number to be allocated to the different BN.

Note that: in the above example, XML is designated for the data type in the data field coming after the data field which designate where in the ADF the second measurement value appears. That is, the DD of the data field is set at a value (0x06) indicating that the data type is described, the CD thereof is set at an ascii code (0x10), the DV thereof is set with "XML". In this way, it is designated that the second measurement value is described in XML. In this case, XML description for the second measurement value is defined separately.

Note that, in the explanation herein, it is defined where in the data fields the measurement values appear; however, the designation may be omitted in cases where the arrangement for the measurement value in the DV for the data communication and the arrangement for the measurement value in the communication information for the registration of the BN are the same and it is possible to judge the data length of each of the measurement values, because it is possible to specify the locations by sequentially adding the data lengths.

[Request Communication from HCD Application]

The following explains a sequence in which the HCD application request the HMD application for data.

A case of inquiry communication request from the HCD application will be described.

Process steps carried out by the HCD application are as follows.

a) Set the communication identifier of the AH such that it represents request communication.

b) Set a value in the sequence number of the AH.

c) Set the service identifier of the AH such that it represents inquiry communication.

d) Describe an inquiry communication item in the ADF.

e) Transmit the data frame to the HMD application.

f) Wait for reception of response communication from the HMD application.

g) When receiving the response communication from the HMD application, the HCD application carries out error check thereof. In cases where there is found no error, the HCD application checks the values of the sequence number and the service identifier of the AH so as to recognize that the response communication corresponds to what request communication.

h) Check the content of the ADF.

Meanwhile, process steps carried out by the HMD application are as follows.

a) When receiving the data frame from the HCD application, the HMD application carries out error check thereof.

b) Check the identifiers of the AH.

c) Read out the ADF and check the inquiry field.

d) In cases where the inquiry target has a time attribute and a measurement time is designated in the inquiry field, the HMD application retrieves the value of inquiry target information having a measurement time coming before and closest to the designated measurement time. In cases where no measurement time is designated, the most recent value is retrieved. The inquiry target may be an operation condition, a measurement condition, or the like, each of which has no time attribute.

e) Set the communication identifier of the AH such that it represents response communication.

f) Set a value in the sequence number of the AH.

g) Set, in the service identifier, the same value of that in the AH of the received data frame.

h) Carry out a judgment process.

i) Set an error check identifier and a judgment process result in the V field coming first in the ADF.

j) Set a predetermined data field in the subsequent data field.

k) Transmit the data frame to the HCD application.

[Setting Communication]

The following explains a sequence of setting communication for setting data or an operation condition.

Figure 14:
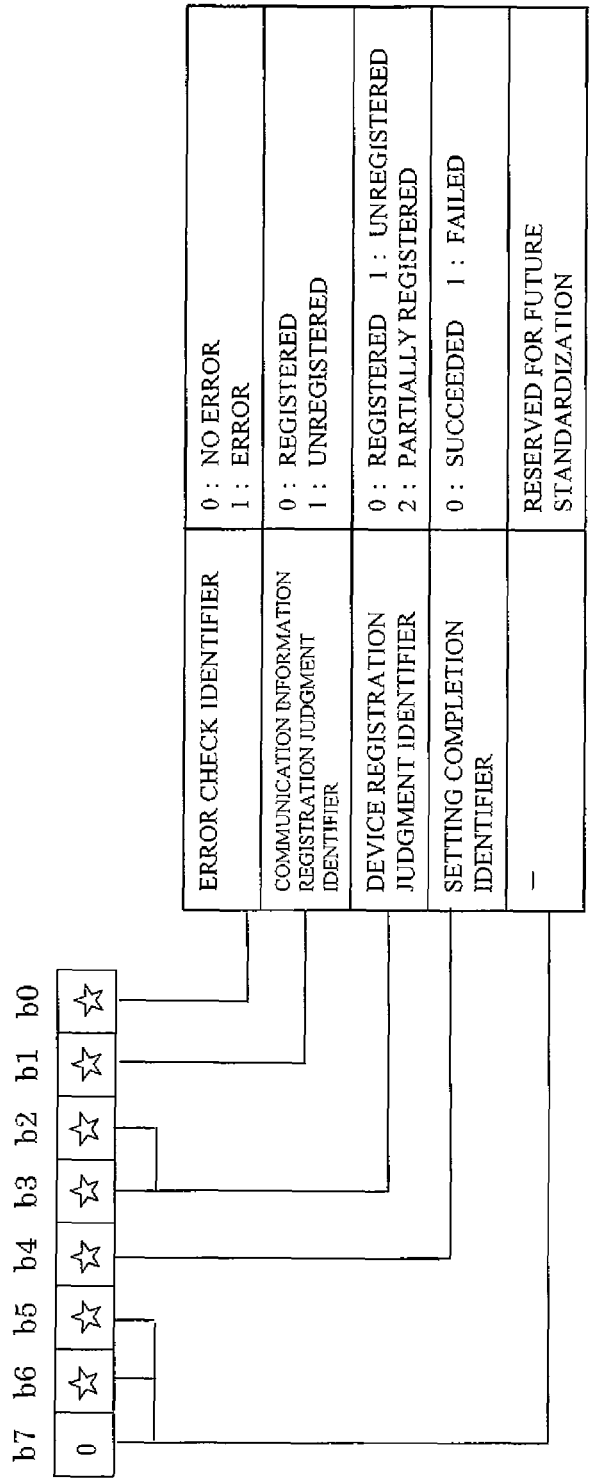
FIG. 14 is a diagram illustrating a sequence of bits representing data items of a V field used for the setting communication in the embodiment of the present invention.

FIG. 13 illustrates a bit sequence representing data items of the first byte of the AH used in the present sequence. FIG. 14 illustrates a bit sequence representing data items of a V field used in the present sequence.

Process steps carried out by a source AE in the setting communication are as follows.

1) Set the communication identifier of the AH such that it represents the setting communication.
2) Set a value in the sequence number of the AH.
3) Set the service identifier of the AH in accordance with the content of setting for a target AE.
4) Describe, in the ADF, the content of setting for the target AE.
5) Transmit the data frame to the target AE.
6) In cases where no setting complete communication is received from the target AE or where error check on the setting complete communication is wrong, the data frame having the same content may be transmitted repeatedly.
7) When receiving the setting complete communication from the target AE, the source AE carries out error check thereof. In cases where there is found no error, the source AE checks the values of the sequence number and the service identifier of the AH so as to recognize that the setting complete communication corresponds to what setting communication.

Process steps carried out by the target AE in the setting communication are as follows.

1) When receiving the data frame, the target AE carries out error check thereof.
2) Check the identifiers of the AH.
3) Read out the content of the setting, and carries out a relevant setting process.
4) Carry out a judgment process.
5) Set the communication identifier of the AH such that it represents the setting complete communication.
6) Set a value in the sequence number of the AH.
7) Set, in the service identifier, the same value of that in the AH for the setting communication.
8) Set the error check content in the ADF.
9) Transmit the data frame to the source AE.

Note that the judgment process herein further includes a step of judging whether or not the setting has been done as described in the readout setting content.

Note that the setting may be made from the HCD application to the HMD application, or from the HMD application to the HCD application. Examples of the setting from the HCD application to the HMD application include a setting of a measurement condition and a setting of an operation condition. Examples of the setting from the HMD application to the HCD application include settings for data and an operation condition, such as registration to the external server and an updating operation of the HMD application.

As described above, the health measuring device and the health control device according to the present embodiment are configured such that a plurality of measurement values are sequentially designated with one BN in the communication information registration communication, so that it is possible to freely correlate the BN with the arrangement of a plurality of measurement values and to efficiently transfer measurement data made up of the plurality of measurement values.

This makes it possible for the HCD application to effectively make a request for the HMD application by designating the BN.

Further, this makes it possible for the HCD application or the HMD application to effectively set an operation condition or data by designating the BN.

Note that, the correlation between the BN and the arrangement of the plurality of measurement values should be unique in the same UDN. Hence, different UDNs are managed in accordance with manufactures or models, so that it is possible to freely correlate a BN with an arrangement of a plurality of measurement values in accordance with manufacturers and models.

Further, it is possible to designate a data type referring to an external standard or designate data using XML.

In addition, by adding the reserved words for the communication information registration such that description using a BN having been transmitted before can be made in correlating one BN with a plurality of measurement values in the communication information registration communication, it is possible that the BN is correlated with a group of frequently used measurement values or the like and is therefore reused. This simplifies the communication information.

Further, UDN, an arrangement of measurement values to be correlated with a BN, and attributes thereof may be configured to be acquired from the external server 300 such that a health measuring device having a poor storage area does not carry out communication information registration communication and transmits a predetermined BN and a plurality of measurement values to the health control device.

<Appendix>

The present invention is not limited to the description of the embodiments above, but may be altered by a skilled person within the scope of the claims. An embodiment based on a proper combination of technical means disclosed in different embodiments is encompassed in the technical scope of the present invention.

Finally, the blocks of the information acquiring device 100 and the measurement data communication device 200, especially the control section 107 and the control section 206, may be constituted by hardware logic, or may be realized by software with the use of a CPU as follows.

That is, each of the information acquiring device 100 and the measurement data communication device 200 includes (i) a CPU (central processing unit) for executing instructions of a control program realizing each function; (ii) a ROM (read only memory) storing the above program; (iii) a RAM (random access memory) for expanding the program; (iv) a storage device (storage medium), such as a memory, storing the program and various types of data; and the like. Therefore, the object of the present invention is achieved by: (i) providing, in each of the information acquiring device 100 and the measurement data communication device 200, a storage medium which stores a program code (executable program, intermediate code program, source program) of the control program of the each of the information acquiring device 100 and the measurement data communication device 200 that is software for realizing the function, and (ii) causing a computer (CPU, or MPU) to read out and execute the program code stored in the storage medium.

Examples of the storage medium are: tapes such as a magnetic tape and a cassette tape; magnetic disks such as a floppy® disk and a hard disk; disks such as a CD-ROM (compact disk read only memory), a magnetic optical disk (MO), a mini disk (MD), a digital video disk (DVD), and a CD-Recordable (CD-R); and the like. Further, the storage medium may be: a card such as an IC card or an optical card; or a semiconductor memory such as a mask ROM, an EPROM (electrically programmable read only memory), EEPROM (electrically erasable programmable read only memory), or a flash ROM.

Further, each of the information acquiring device 100 and the measurement data communication device 200 may be so arranged as to be connectable to a communication network, and the program code may be supplied to each of them via the network. The communication network is not particularly limited. Specific examples thereof are: the Internet, intranet, extranet, LAN (local area network), ISDN (integrated services digital network), VAN (value added network), CATV (cable TV) communication network, virtual private network, telephone network, mobile communication network, satellite communication network, and the like, Further, a transmission medium (channel) constituting the communication network is not particularly limited. Specific examples thereof are: (i) a wired channel using an IEEE1394, a USB (universal serial bus), a power-line communication, a cable TV line, a telephone line, a ADSL line, or the like; or (ii) a wireless channel using IrDA, infrared rays used for a remote controller, Bluetooth®, IEEE802.11, HDR (High Data Rate), a mobile phone network, a satellite connection, a terrestrial digital network, or the like. Note that the present invention can be realized by a form of a computer data signal (a series of data signals) embedded in a carrier wave realized by electronic transmission of the program code.

A measurement data communication device according to the present invention includes: communication information generating means for generating communication information in accordance with (i) an attribute definition column defining attributes of the plurality of measurement values, and (ii) a code value corresponding to the attribute definition column; measurement data generating means for generating measurement data in accordance with the code value and the plurality of measurement values; and transmitting means for transmitting the communication information and the measurement data to the information acquiring device.

Further, an information acquiring device according to the present invention includes: receiving means for receiving (1) communication information including (i) an attribute definition column defining attributes of the plurality of measurement values and (ii) a code value corresponding to the attribute definition column, and (2) measurement data including the plurality of measurement values and the code value; attribute definition extracting storage means for extracting the attribute definition column and the code value from the received communication information and stores the attribute definition column and the code value thus extracted; and measurement value extracting means for acquiring, from the attribute definition extracting storage means, the attribute definition column corresponding to the code value, and extracting the plurality of measurement values from the received measurement data by using the attribute definition column.

Further, a system according to the present invention includes: the measurement data communication device; and the information acquiring device.

This makes it possible to (i) express, with one code, attributes to a plurality of measurement items of measurement data for each measurement device; (ii) employ a different code system according to a type of measurement device; (iii) allow for free addition of a new measurement item; and the like.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

What is claimed is:

1. A measuring data communication device for measuring a health condition of an examinee and transmitting a plurality of measurement values representing a result of the measurement, to an information acquiring device managing the measurement values, said measuring data communication device, comprising:
    communication information generating section configured to generate communication information, the communication information including a code value and an attribute definition column corresponding to the code value, the attribute definition column including attribute definitions of measurement values for each of the plurality of measurement values;
    measurement data generating section for generating measurement data in accordance with the code value and the plurality of measurement values; and
    transmitting section for transmitting the communication information and the measurement data to the information acquiring device.

2. The measurement data communication device of claim 1, wherein
    the communication information is initially transmitted and registered with the information acquiring device and the communication information is not transmitted after it is registered.

3. The measurement data communication device of claim 1, wherein each attribute of the attribute definition column corresponds to a respective code value.

4. The measurement data communication device of claim 3, wherein in the communication information, (i) a BN (byte name which is an identifier for uniquely identifying a communication item designated by UDN) designated by UDN (unique device name), (ii) the name of a communication item correlated with the BN, (iii) a unit, and (iv) a scale are associated with respective code values.

5. An information acquiring device for (i) receiving, from a measurement data communication device that measures a plurality of measurement values, a plurality of measurement values measured by the measurement data communication device and representing a health condition of an examinee and (ii) managing the plurality of measurement values,
    said information acquiring device, comprising:
    receiving section for receiving (1) communication information including a code value and an attribute definition column corresponding to the code value, the attribute definition column including attribute definitions of measurement values for each of the plurality of measurement values, and (2) measurement data including the plurality of measurement values and the code value;
    attribute definition extracting storage section for extracting the attribute definition column and the code value from the received communication information and storing the attribute definition column and the code value thus extracted; and
    measurement value extracting section for acquiring, from the attribute definition extracting storage section, the attribute definition column corresponding to the code value, and extracting the plurality of measurement values from the received measurement data by using the attribute definition column.

6. The information acquiring device of claim 5, wherein:
    the communication information is initially received from the measurement data communication device and registered in the attribute definition extracting storage section and the communication is not received after it is registered.

7. The information acquiring device of claim 5, wherein each attribute of the attribute definition column corresponds to a respective code value.

8. The information acquiring device of claim 7, wherein in the communication information, (i) a BN (byte name which is an identifier for uniquely identifying a communication item out of communication items designated by UDN) designated by UDN (unique device name), (ii) the name of a communication item correlated with the BN, (iii) a unit, and (iv) a scale are associated with respective code values.

9. A system, comprising:
a measuring data communication device for measuring a health condition of an examinee and transmitting a plurality of measurement values representing a result of the measurement, to an information acquiring device managing the measurement values; and
an information acquiring device for (i) receiving, from the measurement data communication device, the plurality of measurement values measured by the measurement data communication device and (ii) managing the plurality of measurement values,
said measuring data communication device, including:
communication information generating section configured to generate communication information, the communication information including a code value and an attribute definition column corresponding to the code value, the attribute definition column including attribute definitions of measurement values for each of the plurality of measurement values;
measurement data generating section for generating measurement data in accordance with the code value and the plurality of measurement values; and
transmitting section for transmitting the communication information and the measurement data to the information acquiring device,
said information acquiring device, including:
receiving section for receiving (1) the communication information including a code value and an attribute definition column corresponding to the code value, the attribute definition column including attribute definitions of measurement values for each of the plurality of measurement values;
attribute definition extracting storage section for extracting the attribute definition column and the code value from the received communication information and storing the attribute definition column and the code value thus extracted; and
measurement value extracting section for acquiring, from the attribute definition extracting storage section, the attribute definition column corresponding to the code value, and extracting the plurality of measurement values from the received measurement data by using the attribute definition column.

10. A measuring data communication device for measuring a health condition of an examinee and transmitting a plurality of measurement values representing a result of the measurement, to an information acquiring device managing the measurement values, said measuring data communication device, comprising:
communication information generating section configured to generate communication information, the communication information including a code value and an attribute definition column corresponding to the code value, the attribute definition column including attribute definitions of the measurement values for each of the plurality of measurement values, the attribute definitions including at least attribute names;
measurement data generating section for generating measurement data in accordance with the code value and the plurality of measurement values; and
transmitting section for transmitting the communication information and the measurement data to the information acquiring device.

11. An information acquiring device for (i) receiving, from a measurement data communication device that measures a plurality of measurement values, a plurality of measurement values measured by the measurement data communication device and representing a health condition of an examinee and (ii) managing the plurality of measurement values,
said information acquiring device, comprising:
receiving section for receiving (1) communication information including a code value and an attribute definition column corresponding to the code value, the attribute definition column including attribute definitions of the measurement values for each of the plurality of measurement values, the attribute definitions including at least attribute names, and (2) measurement data including the plurality of measurement values and the code value;
attribute definition extracting storage section for extracting the attribute definition column and the code value from the received communication information and storing the attribute definition column and the code value thus extracted; and
measurement value extracting section for acquiring, from the attribute definition extracting storage section, the attribute definition column corresponding to the code value, and extracting the plurality of measurement values from the received measurement data by using the attribute definition column.

12. A system, comprising:
a measuring data communication device for measuring a health condition of an examinee and transmitting a plurality of measurement values representing a result of the measurement, to an information acquiring device managing the measurement values; and
an information acquiring device for (i) receiving, from the measurement data communication device, the plurality of measurement values measured by the measurement data communication device and (ii) managing the plurality of measurement values,
said measuring data communication device, including:
communication information generating section configured to generate communication information, the communication information including a code value and an attribute definition column corresponding to the code value, the attribute definition column including attribute definitions of the measurement values for each of the plurality of measurement values, the attribute definitions including at least attribute names;
measurement data generating section for generating measurement data in accordance with the code value and the plurality of measurement values; and
transmitting section for transmitting the communication information and the measurement data to the information acquiring device,
said information acquiring device, including:
receiving section for receiving (1) the communication information including a code value and an attribute definition column corresponding to the code value, the attribute definition column including attribute definitions of the measurement values for each of the plurality of measurement values, the attribute definitions including at least attribute names;
attribute definition extracting storage section for extracting the attribute definition column and the code value from the received communication information and storing the attribute definition column and the code value thus extracted; and measurement value extracting section for acquiring, from the attribute definition extracting storage section, the attribute definition column corresponding to the code value, and extracting the plurality of measurement values from the received measurement data by using the attribute definition column.

* * * * *